(12) United States Patent
Avitan

(10) Patent No.: US 10,586,623 B2
(45) Date of Patent: *Mar. 10, 2020

(54) PATIENT CARE DEVICE AND SYSTEM FOR SERVICE TO INDIVIDUALS WITH DIMINISHING DEXTERITY AND NEUROLOGICAL PHYSIOLOGICAL FUNCTIONALITY

(71) Applicant: LIVECARE CORP., New York, NY (US)

(72) Inventor: Peri Avitan, New York, NY (US)

(73) Assignee: LIVECARE CORP., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/291,860

(22) Filed: Mar. 4, 2019

(65) Prior Publication Data

US 2019/0259268 A1  Aug. 22, 2019

Related U.S. Application Data

(63) Continuation-in-part of application No. 16/278,977, filed on Feb. 19, 2019, and a continuation-in-part of (Continued)

(51) Int. Cl.
*G16H 80/00* (2018.01)
*G06Q 50/18* (2012.01)
(Continued)

(52) U.S. Cl.
CPC .............. *G16H 80/00* (2018.01); *A61B 5/00* (2013.01); *A61B 5/0024* (2013.01); *A61B 5/0205* (2013.01); *A61B 5/1117* (2013.01); *A61B 5/681* (2013.01); *A61B 5/6822* (2013.01); *A61B 5/742* (2013.01); *A61B 5/7405* (2013.01); *G06Q 50/188* (2013.01); *G08B 21/0269* (2013.01); *G08B 21/043* (2013.01); *G08B 21/0453* (2013.01); *G08B 25/016* (2013.01);

(Continued)

(58) Field of Classification Search
None
See application file for complete search history.

(56) References Cited

U.S. PATENT DOCUMENTS

| 8,181,051 B2 * | 5/2012 | Barth | G06F 1/3203 |
| | | | 713/323 |
| 8,433,281 B1 * | 4/2013 | Blum | H04W 4/90 |
| | | | 455/404.1 |

(Continued)

*Primary Examiner* — Fekadeselassie Girma
(74) *Attorney, Agent, or Firm* — Hulsey PC

(57) ABSTRACT

A patient care device includes an attachment element configured to physically attach the device to a patient, such that the device can be worn around the patient's neck as a pendant. The device may further comprise a communication system configured to enable voice and visual communication through the device, and an emergency activation system configured to indicate a potential emergency situation of the patient. The emergency activation system may comprise at least one of a mechanical trigger system, a virtual trigger system, a fall detection system, a location tracking system, a bio monitoring system or a combination thereof.

18 Claims, 28 Drawing Sheets

Related U.S. Application Data application No. 16/252,607, filed on Jan. 19, 2019, and a continuation-in-part of application No. 15/608,972, filed on May 30, 2017, now abandoned.

(60) Provisional application No. 62/796,566, filed on Jan. 24, 2019, provisional application No. 62/361,678, filed on Jul. 13, 2016, provisional application No. 62/327,997, filed on Apr. 26, 2016, provisional application No. 62/315,102, filed on Mar. 30, 2016.

(51) Int. Cl.

| | | |
|---|---|---|
| *G16H 40/67* | (2018.01) | |
| *A61B 5/00* | (2006.01) | |
| *A61B 5/0205* | (2006.01) | |
| *G08B 21/04* | (2006.01) | |
| *H04Q 9/00* | (2006.01) | |
| *A61B 5/11* | (2006.01) | |
| *G08B 21/02* | (2006.01) | |
| *G08B 25/01* | (2006.01) | |
| *G08B 25/10* | (2006.01) | |
| *G08B 27/00* | (2006.01) | |
| *H04W 4/90* | (2018.01) | |
| *A61B 5/021* | (2006.01) | |
| *A61B 5/024* | (2006.01) | |
| *A61B 5/145* | (2006.01) | |

(52) U.S. Cl.
CPC ........... *G08B 25/10* (2013.01); *G08B 27/005* (2013.01); *G16H 40/67* (2018.01); *H04Q 9/00* (2013.01); *A61B 5/021* (2013.01); *A61B 5/024* (2013.01); *A61B 5/1112* (2013.01); *A61B 5/14532* (2013.01); *A61B 5/14542* (2013.01); *H04Q 2209/43* (2013.01); *H04W 4/90* (2018.02)

(56) References Cited

U.S. PATENT DOCUMENTS

| | | | | |
|---|---|---|---|---|
| 9,008,666 B1* | 4/2015 | Reeves | ............ | H04W 36/0072 370/332 |
| 10,271,620 B1* | 4/2019 | Dickson | ............. | A44C 15/0015 |
| 2003/0114764 A1* | 6/2003 | Masuda | .................. | A61B 5/02 600/490 |
| 2005/0212760 A1* | 9/2005 | Marvit | .................. | G06F 1/1613 345/156 |
| 2005/0225964 A1* | 10/2005 | Simoni | ................ | A01K 27/006 362/103 |
| 2007/0218866 A1* | 9/2007 | MacIver | ................ | H04M 11/04 455/404.1 |
| 2007/0276600 A1* | 11/2007 | King | ...................... | G08G 1/042 701/301 |
| 2009/0010249 A1* | 1/2009 | Gass | .................... | H04L 61/2015 370/352 |
| 2009/0160643 A1* | 6/2009 | Lizza | ................ | G08B 21/0415 340/540 |
| 2010/0291894 A1* | 11/2010 | Pipes | .................... | H04W 4/029 455/404.2 |
| 2012/0154957 A1* | 6/2012 | Williams | ................ | H02H 1/06 361/1 |
| 2012/0303548 A1* | 11/2012 | Johnson | ................ | G06Q 40/04 705/36 R |
| 2013/0090083 A1* | 4/2013 | DeMont | .............. | G08B 21/043 455/404.2 |
| 2014/0091934 A1* | 4/2014 | Vallance | ............ | G08B 21/0446 340/573.1 |
| 2014/0171152 A1* | 6/2014 | Dempsey | .......... | H04M 1/72536 455/564 |
| 2014/0321362 A1* | 10/2014 | Pipes | .................... | H04W 4/029 370/328 |
| 2015/0009654 A1* | 1/2015 | Chan | .................... | H05B 33/086 362/104 |
| 2015/0317893 A1* | 11/2015 | Tseng | ................ | H04M 1/72522 340/686.1 |
| 2016/0055739 A1* | 2/2016 | Larson | .................. | G08B 21/24 340/539.13 |
| 2016/0093196 A1* | 3/2016 | Shinar | .................. | A61B 5/6892 340/565 |
| 2016/0135431 A1* | 5/2016 | Sheldon | ................ | H02J 7/0047 119/859 |
| 2017/0038792 A1* | 2/2017 | Moore | ............. | A61B 5/02438 |
| 2017/0180964 A1* | 6/2017 | Mehta | ............. | H04W 4/90 |
| 2017/0270507 A1* | 9/2017 | Wang | .................... | G06Q 20/32 |
| 2017/0316675 A1* | 11/2017 | Bauer | ................ | H04L 67/1097 |
| 2018/0184236 A1* | 6/2018 | Faraone | ................ | H04W 4/026 |
| 2019/0021458 A1* | 1/2019 | Guan | ...................... | A44C 5/00 |
| 2019/0147721 A1* | 5/2019 | Avitan | ................ | G08B 21/043 340/573.1 |
| 2019/0192075 A1* | 6/2019 | Kranz | ..................... | A61B 5/746 |
| 2019/0214153 A1* | 7/2019 | Avitan | ................ | A61B 5/6822 |
| 2019/0254523 A1* | 8/2019 | Avitan | ................ | A61B 5/742 |
| 2019/0259268 A1* | 8/2019 | Avitan | ..................... | H04Q 9/00 |
| 2019/0261153 A1* | 8/2019 | Avitan | ................... | G16H 40/67 |
| 2019/0282127 A1* | 9/2019 | Nikolova-Simons | ........................ | A61B 5/746 |
| 2019/0350457 A1* | 11/2019 | Avitan | ................ | A61B 5/7405 |

* cited by examiner

← Create Account

First Name

Last Name

Email    —1306

Password

Confirm Password

Address 1

Address 2

City

State

FIG. 13C

PATIENT CARE DEVICE AND SYSTEM FOR SERVICE TO INDIVIDUALS WITH DIMINISHING DEXTERITY AND NEUROLOGICAL PHYSIOLOGICAL FUNCTIONALITY

CROSS-REFERENCE TO RELATED APPLICATIONS

This Application claims benefit to Provisional application 62/796,566 filed Jan. 24, 2019; and is a CIP of application Ser. No. 16/278,977 filed Feb. 29, 2019, application Ser. No. 16/252,607 filed Jan. 19, 2019, and application Ser. No. 15/608,972, filed May 30, 2017 which claims benefit to Provisional Application No. 62/361,678 filed Jul. 13, 2016, Provisional Application 62/327,997 filed Apr. 26, 2016, and Provisional Application 62/315,102 filed Mar. 30, 2016. All of the aforementioned applications are incorporated herein by this reference.

A portion of the disclosure of this patent document contains material which is subject to copyright protection. The copyright owner has no objection to the facsimile reproduction by anyone of the patent document of the patent disclosure, as it appears in the Patent and Trademark Office patent file or records, but otherwise reserves all copyright rights whatsoever.

FIELD OF THE DISCLOSURE

This disclosure is generally directed to an emergency response device and method, according to various embodiments.

BACKGROUND OF THE DISCLOSURE

Providing proper and efficient care for individuals such as seniors or other patients who may suffer from diminishing dexterity and neurological physiological functionality may be difficult and financially burdensome. Additionally, providing live-in care for such individuals, or residence in a specialized care facility may be undesirable and invasive for both patients and their families. As such, an improved system for providing care and/or assistance to such individuals is needed.

SUMMARY OF THE DISCLOSURE

Various inventive features are described below that can each be used independently of one another or in combination with other features.

The present disclosure relates to a smart emergency response device, which may include an emergency activation system; a visual screen; and a voice communication element. In some embodiments, the device may be configured to establish wireless communication between a remote response agent and a user of the device, via the emergency activation system. In some embodiments, the emergency activation system may include at least one of a mechanical trigger, a fall detector, a location tracking member, a bio-signs receiver, or a combination thereof. In certain embodiments establishing communication with the remote response agent enables voice communication and visual communication between the user and the response agent.

In some embodiments, the emergency activation system is configured to sense a potential emergency situation of the user and cause an emergency alert to be sent to the response agent upon sensing said potential emergency situation, said emergency activation system including the mechanical trigger, wherein physical activation of the mechanical trigger causes said emergency alert to be sent. In other embodiments, the emergency activation system further comprises the fall detector, said fall detector configured to detect a fall motion of the device, wherein detection of said fall motion causes said emergency alert to be sent. In further embodiments, the emergency activation system further comprises the location tracking member, wherein said location tracking member is configured to determine a location of the device, wherein detection of a location outside an expected region causes said emergency alert to be sent. In other embodiments, the emergency activation system further comprises the bio-signs receiver, wherein said bio signs receiver is configured to receive the user's bio signs, wherein detection of abnormal bio signs causes said emergency alert to be sent.

In some embodiments, the emergency activation system is further responsive to a touch command via said visual screen and/or a voice command via the voice communication element. In further embodiments, the device is wearable by the user. In yet further embodiments, the device is configurable for wireless communication with a plurality of vital monitors.

Also disclosed, according to various embodiments, is an emergency response system, which may comprise: an emergency response device including: an emergency activation system; a non-emergency communication system; a visual touch screen system; a voice communication system; and a wireless data transmission system, wherein the emergency activation system is configured to detect a potential emergency situation of a user of the device and, upon detection, cause an emergency alert to be sent via said wireless data transmission system, wherein said emergency activation system comprises at least one of a mechanical trigger system, a fall detection system, a location tracking system, a bio monitoring system or a combination thereof, for detecting said emergency situation.

In some embodiments, the emergency alert is sent to a dedicated response agent of the emergency response system and/or a caretaker of the user. In further embodiments, the response system further comprises a response agent system, the response agent system dedicated to receiving and responding to emergency alerts. In some embodiments, the non-emergency communication system is configured to provide information associated with the user's medical needs. In some embodiments, the mechanical trigger system is configured to be actuated via mechanical activation of a physical trigger, wherein said mechanical activation causes said emergency alert to be sent, said fall detection system is configured to detect a fall motion of the device, wherein detection of said fall motion causes said emergency alert to be sent, said location tracking system is configured to determine a location of the device, wherein detection of a location outside an expected region causes said emergency alert to be sent, said bio monitoring system is configured to detect a patient's bio signs, wherein detection of abnormal bio signs causes said emergency alert to be sent, and, wherein said emergency activation system comprises said mechanical trigger system in combination with at least one of said fall detection system, location tracking system, and bio monitoring system.

In other embodiments, the device is configurable for wireless communication with a plurality of vital monitors. In some embodiments, said device is wearable by the user as a watch or pendant.

Also disclosed, according to various embodiments, is an emergency response method, which may comprise a) monitoring to determine whether an emergency alert has been sent by an emergency response device, the emergency response devise associated with a user and comprising: a wireless data transmission system, an emergency activation system configured to detect a potential emergency situation of the user of the device and, upon detection, cause an emergency alert to be sent via the wireless data transmission system, a visual screen and/or camera, and a voice communication system; and b) upon determination that an emergency alert has been sent, responding to the emergency alert, via audio and visual communication with the user, wherein said emergency activation system comprises at least one of a mechanical trigger system, a virtual trigger system, a fall detection system, a location tracking system, a bio monitoring system or a combination thereof, for detecting said potential emergency situation.

In some embodiments, visual communication with the user comprises transmitting video content to be viewed by the user on said screen and/or receiving video content through said camera.

In some embodiments, said mechanical trigger system is configured to be actuated via mechanical activation of a physical trigger in the device, wherein said mechanical activation causes said emergency alert to be sent, said virtual trigger system is configured to be actuated via touch screen activation of a virtual emergency activation element, said visual screen being a touch sensitive screen, wherein said touch screen activation causes said emergency alert to be sent, said fall detection system is configured to detect a fall motion of the device, wherein detection of said fall motion causes said emergency alert to be sent, said location tracking system is configured to determine a location of the device, wherein detection of a location outside an expected region causes said emergency alert to be sent, said bio monitoring system is configured to detect a patient's bio signs, wherein detection of abnormal bio signs causes said emergency alert to be sent, and wherein said emergency activation system comprises at least three of said mechanical trigger system, virtual trigger system, fall detection system, location tracking system, and bio monitoring system.

In some embodiments, the device further comprises a non-emergency communication system. In further embodiments, the method further comprises communicating information related to the medical needs of the patient via said non-emergency communication system.

Additionally, in accordance with various embodiments, disclosed is a patient care method which may comprise: monitoring the status of multiple patients, and responding to the needs of said multiple patients by a response agent system; wherein each of said multiple patients is an enrolled participant of the response agent system; wherein the response agent system is configured to receive communications regarding said patient needs as they arise and to convey said communications to multiple response agents of said response agent system as said needs are received; wherein responding to the needs of said multiple patients comprises responding by an available response agent of said multiple response agents to any one of said needs as the need is conveyed.

In embodiments, each arising need is regarded as a pending need until a response is rendered, the method further comprising indicating by a response agent that a response to a pending need has been rendered, whereupon said need is no longer regarded as pending. In some embodiments, said communications regarding said patient needs are received from a patient care device maintained by a patient of said multiple patients. In further embodiments, said communications regarding said patient needs are displayed via a response agent interface system, which is accessible to each of said multiple response agents through a communication network. In yet further embodiments, monitoring the status of multiple patients, and responding to the needs of said multiple patients by a response agent system comprises response agent interaction through said display of the response agent interface system.

In embodiments, patient needs comprise emergency assistance needs and/or non-emergency needs. In some embodiments, monitoring the status of multiple patients is preformed on an as-needed basis and comprises at least one of: monitoring for an emergency alert status of a patient, monitoring a location a patient, monitoring activity of a patient, monitoring medication needs a patient, monitoring bio signs of a patient, and monitoring non-emergency requests of a patient; and responding to patient needs is performed on an as needed basis, and comprises at least one of: responding to an emergency alert, responding to a non-emergency request, responding to an anticipated need of a patient, communicating with a patient, sending assistance to a patient, and contacting and/or connecting the patient with a third party.

In some embodiments, each of said multiple patients resides in a private residence. In further embodiments, said multiple patients reside in a common care facility.

Also disclosed in accordance with various embodiments, is a patient care method which may comprise a response agent system, the response agent system comprising: an active alerts system configured indicate emerging and/or pending needs of multiple patients as they arise in real time, wherein said multiple patients are established participants of the response agent system; a response contact system configured to enable said response agents to view said emerging and/or pending patient needs, wherein any one of said response agents can render a response to said emerging and/or pending patient need; wherein a responding agent can indicate that a response has been rendered; and wherein the active alerts system is further configured to remove said emerging and/or pending patient need from being indicated as such and/or indicate that a response has been rendered upon an indication from said responding agent that a response has been rendered.

In some embodiments, the method further comprises a response agent interface system, configured to enable monitoring a status of said multiple patients by the multiple response agents through a display of the response agent interface system, wherein the display is configured to indicate said emerging and/or pending needs through said active alerts system, wherein said display is commonly accessible by the multiple response agents via a communications network. In further embodiments, the response agent interface system is configured to enable accessing and/or viewing information regarding any one of said multiple patients, said information comprising at least one of a location of a patient, medication needs a patient, and bio signs of a patient. In yet further embodiments, the response agent interface system is configured to enable said response agents to preform at least one of: indication of an acceptance of an alert; establishing communication with a patient; sending and/or setting a reminder for a patient; locating a patient; and monitoring bio signs of a patient.

In some embodiments, said response contact system is further configured to enable communication between said multiple patients and response agents, wherein said communication includes audio, video, text messaging, communication through said response agent interface system, or combinations thereof.

In further embodiments, the method further comprises a unilateral monitoring contact system configured to enable said multiple response agents to send and/or set reminders and/or notifications to be communicated to the patient. In yet further embodiments, of the multiple response agents is located in a common facility. In yet further embodiments, said multiple response agents are located remotely from one another.

In some embodiments, said emerging and/or pending patient needs comprise emergency alerts and/or non-emergency alerts. In further embodiments, said emerging and/or pending patient needs are conveyed through a patient care device which is in a patient's possession.

In embodiments, said emerging and/or pending patient needs are transmitted from the patient care device to the response agent system in response to an indication of possible patient distress and/or danger automatically detected by the device. In some embodiments, said device includes at least one sensor incorporated within said device and/or in communication with said device, wherein said sensor is configured to sense said indication of possible patient distress and/or danger. In further embodiments, said sensor comprises a fall sensor, a position tracking device, and/or a bio monitor device. In some embodiments, the method further comprises enabling patient interaction with personal contacts, such as friends and family, social groups, and the like, through the device.

Also disclosed, according to various embodiments, is an emergency response method which may comprise: providing a device for establishing communication with a remote response agent, the device comprising an emergency activation element a visual screen, and a voice communication element; wherein the device is configured for establishing wireless communication between a remote response agent and a user of the device via said emergency activation element, wherein said emergency activation element comprises at least one of an activation button, a touch sensor in the visual screen, an audio trigger, a motion sensor, or a combination thereof, and wherein establishing communication with said remote response agent enables voice communication and visual communication between the user and response agent.

In further embodiments, the device is wearable as a pendant or watch. In further embodiments, the device further comprises a location-tracking element. In yet further embodiments, establishing communication further enables location tracking of the user by the response agent.

In some embodiments, the device is configured to send a communication to said response agent and/or to a third party based on information regarding a location of the user, said information regarding location received from the location tracking element. In further embodiments, the device is configured to send an alert communication to said response agent and/or third party upon information that the user is outside a designated location.

In some embodiments, said emergency activation element further comprises a vital signal receiver in communication with at least one vital monitor, said vital monitor being configured to monitor a vital signal of the user of said device, wherein said emergency activation element is triggered upon detection of an abnormal vital signal by said user. In further embodiments, said device is configurable for wireless communication with a plurality of vital monitors. In further embodiments, information based on said signals received from said plurality of vital monitors is transmittable to said response agent, and/or a designated third party.

In some embodiments, the device further comprises a health diagnostic module configured to indicate the user's health status based on the collective signals received from said plurality of vital monitors. In some embodiments said plurality of vital monitors comprise a blood pressure sensor, a fall detector sensor, a blood sugar sensor, a heart signal monitor, or combination thereof. In further embodiments the device is configurable for wireless communication with at least one other party different from said response agent. In yet further embodiments the device is further configured to display the user's personal information on the visual screen.

In some embodiments, said personal information comprises voice and or visual communication received from third party members and/or recorded by the user. In further embodiments the visual screen is configured to display said personal information according to personal information categories, said categories comprising reminders associated with medical needs, reminders associated with personal needs, visual communications from friends and/or family members.

In some embodiments the device is configured for engagement of services related to elderly care, wherein said device is configured to display a categorized compilation of service providers available on an as needed basis, according to at least one service category, wherein said service providers are available according to a prearranged monetary rate. In some embodiments, the displayed service providers are local to the user and/or user's location. In further embodiments the device is configured to locate said service providers who are within a predetermined distance from the user. In further embodiments, said services related to elderly care comprise medical services, nursing services, home care services, housekeeping services, food preparation services, food delivery services, grocery delivery services, transportation services, or a combination thereof.

Also disclosed, according to various embodiments, is a patient care device which may comprise: an attachment element, configured to physically attach the device to the patient, such that the device can be worn around the patient's neck as a pendant; a communication system configured to enable voice and visual communication through said device; a display screen; an emergency activation system configured to indicate a potential emergency situation of the patient, said emergency activation system comprising at least one of a mechanical trigger system, a virtual trigger system, a fall detection system, a location tracking system, a bio monitoring system or a combination thereof.

In some embodiments, the device has a generally flat rectangular configuration, with a front side and a back side opposite said front side, wherein the display screen is located on the front side. In some embodiments, the attachment element comprises a channel for receiving a lanyard, such that the lanyard can be looped around the patient's neck with the device suspended from the lanyard, wherein a width of the channel is configured to prevent the device from twisting, and to keep the device facing in one direction when suspended by the lanyard and worn around the patient's neck. In some embodiments, the device further comprises a lighting element located on the font side, wherein the lighting element is configured to shine light in front of the patient when the patient is wearing the device with the front side facing forward, such that the lighting element provides illumination for a forward walking path of the patient.

In some embodiments, the device further comprises a lighting control element configured to control an intensity of the lighting element, wherein the lighting control element is operated manually and/or is configured to automatically adjust the illumination intensity in response to ambient conditions.

In some embodiments, the lighting element can be remotely controlled by the lighting control element.

In some embodiments, the device comprises a speaker and microphone located on the front side of the device; and a location tracking element. In some embodiments, the emergency activation system comprises a button, wherein the button is located on the front side of the device. In some embodiments, the device further comprises a lighting element, a speaker, microphone, and at least one camera, which are positioned on the front side of the device.

In further embodiments, the device comprises a lanyard engaged through said channel, wherein said lanyard is configured to loop and the patient's neck for suspending the device, wherein said lanyard is size adjustable and/or sized to position the device to hang around a lower section of the patient's abdomen and/or below the patient's abdomen. In some embodiments, the emergency activation element comprises a mechanical trigger system, said mechanical trigger system comprising a button.

In further embodiments, the device includes a wear detection system, wherein, when the device is not worn by the patient, said wear detection system is configured to provide an indication that the patient is not wearing the device. In some embodiments, voice and visual communication can be automatically enabled through the device without patient activation.

According to various embodiments, also disclosed is patient care system, which may comprise: a patient care device configured to be worn by the patient, comprising: an attachment element, configured to physically attach the device to the patient, a communication system configured to enable voice and visual communication through said device, a display screen, and an emergency activation system configured to indicate a potential emergency situation of the patient, said emergency activation system comprising a mechanical trigger system, and at least one of a virtual trigger system, a fall detection system, a location tracking system, a bio monitoring system; and a response system, configured to monitor for and respond to an indication of a potential emergency situation.

In further embodiments, the device further comprises a lighting element. In some embodiments, the device can be worn as a watch and/or as a pendant. In further embodiments, the device comprises a wear detection system, wherein, when the device is not worn by the patient, said wear detection system is configured to provide an indication that the patient is not wearing the device. In some embodiments, voice and visual communication can be automatically enabled through the device, without patient activation. In some embodiments, the device further comprises a location tracking element.

Also disclosed, according to various embodiments, is a patient care method, comprising: wearing a patient care device, the device comprising: an attachment element, configured enable the device to be worn, a communication system configured to enable voice and visual communication through said device, a display screen, and an emergency activation system configured to indicate a potential emergency situation of the patient, said emergency activation system comprising a mechanical trigger system, and at least one of a virtual trigger system, a fall detection system, a location tracking system, a bio monitoring system.

In some embodiments, wearing the device comprises hanging the device via a lanyard looped around the neck and attached to the device, and positioning the device to hang around a lower section of the abdomen and/or below the abdomen. In some embodiments, the device further comprises a lighting element, wherein the lighting element is positioned at a front side of the device, wherein wearing the device further comprises orienting the device such that the lighting element is forward facing, the method further comprising using the device to provide illumination for a forward walking path.

Also disclosed, according to various embodiments, is a patient care method comprising: remotely monitoring bio-signs of a patient, said bio-signs received from a patient care device associated with the patient, determining a health status of the patient based on said bio-signs received, wherein said patient care device is capable of establishing wireless communication with a plurality of biosensors for receiving bio-signs from said biosensors.

In some embodiments, establishing wireless communication comprises Bluetooth pairing. In some embodiments, said multiple biosensors are independent from said device, and wherein the device further comprises at least one embedded biosensor. In some embodiments, said device is configured for wearing by the patient. In some embodiments, said device is configured for wearing around a wrist or as a neck suspended pendant.

In some embodiments, said multiple biosensors comprise blood pressure sensor, a blood glucose monitor, a heart rate sensor, and oxygen level monitor, or combinations thereof. In further embodiments, the method comprises triggering an emergency alert in response to an indication of a potential emergency situation based on information received from at least one of said biosensors. In some embodiments, the device is further configured to transmit and receive audio, visual, and text communications.

In further embodiments, the method comprises sending information regarding the patient's medical needs for display on a visual screen of the device. In some embodiments, the device further comprises a location tracking element.

Also disclosed according to various embodiments, is a bio-monitoring system which may comprise: a remote monitoring system for monitoring bio-signs of a patient, said bio-signs received from a patient care device associated with the patient, determining a health status of the patient based on said bio-signs received, wherein said patient care device is capable of establishing wireless communication with multiple biosensors for receiving bio-signs from said biosensors, wherein said wireless communication comprises Bluetooth pairing.

In some embodiments, said multiple biosensors are independent from said device, and wherein the device further comprises at least one embedded biosensor. In some embodiments, said device is configured for wearing by the patient around the wrist or as a neck suspended pendant. In some embodiments, said multiple biosensors comprise blood pressure sensor, a blood glucose monitor, a heart rate sensor, and oxygen level monitor, or combinations thereof. In further embodiments, the system comprises an emergency alert system configured for triggering an alert in response to an indication of a potential emergency situation based on information received from at least one of said biosensors.

According to various embodiments, disclosed is a patient care device for monitoring a patient's health status, the device comprising: at least one bio-signs receiver configured to receive bio readings from multiple biosensors, wherein the device is capable of establishing wireless short-range communication with each of said biosensors for receiving bio-signs from each sensor; and a wireless data transmission system for long range data transmission.

In some embodiments, said wireless short-range communication comprises Bluetooth pairing. In some embodiments, said device is configured for wearing by the patient. In some embodiments, said multiple biosensors comprise blood pressure sensor, a blood glucose monitor, a heart rate sensor, and oxygen level monitor, or combinations thereof. In further embodiments, the device further comprises a location tracking element.

Also disclosed, according to various embodiments, is a patient care method which may comprise a service engagement system, the service engagement system comprising: communicating a request for service related to at-home care of a patient to one or more service professionals, wherein the request is made through a patient care device having wireless communication capabilities, wherein said service professionals are in an industry related to the requested service, and meet a specified criteria set in the request; and enabling at least one of said service professionals to accept the request to perform the requested service at the patient's place of residence, wherein the service is performed on the same day the request is made, wherein the service professionals are pre-established enrollees of the service engagement system.

In some embodiments, said service comprises nursing care and/or medical related care. In some embodiments, said service comprises housekeeping help, food preparation, grocery shopping, physical therapy, chiropractic treatment, nursing care and/or medical related care. In some embodiments, a fixed fee is set for performance of the service. In other embodiments, a fee for the service is negotiable. In some embodiments, the fee for the service can be negotiated by a caretaker of the patient. In some embodiments, the request for service can be initiated by the patient and/or by a caretaker of the patient. In some embodiments, the specified criteria set in the request includes proximity of the service provider to the patient. In some embodiments, the patient care device further comprises an emergency response system configured to alert of a potential emergency situation of the patient to a remote response agent. In further embodiments, the patient care device comprises a non-emergency communication system, said non-emergency communication system configured to enable the patient to communicate with third parties and receive information regarding medical needs.

Also disclosed, according to various embodiments, is a service engagement system which may comprise: a request communication system for communicating a request for service related to at-home care of a patient to one or more service professionals, wherein the request is made through a patient care device having wireless communication capabilities, wherein said service professionals are in an industry related to the requested service, and meet a specified criteria set in the request; and a request acceptance system for enabling at least one of said service professionals to accept the request for performing the requested service at the patient's place of residence, wherein the service is performed on the same day the request is made, wherein the service professionals are pre-established enrollees of the service engagement system.

In some embodiments, said service comprises nursing care and/or medical related care. In some embodiments, said service comprises housekeeping help, food preparation, grocery shopping, physical therapy, chiropractic treatment, nursing care and/or medical related care. In some embodiments, a fixed fee is set for performance of the service. In other embodiments, a fee for the service is negotiable. In some embodiments, the fee for the service can be negotiated by a caretaker of the patient. In some embodiments, the request for service can be initiated by the patient and/or by a caretaker of the patient. In some embodiments, the specified criteria set in the request includes proximity of the service provider to the patient. In some embodiments, the patient care device further comprises an emergency response system configured to alert of a potential emergency situation of the patient to a remote response agent. In further embodiments, the patient care device comprises a non-emergency communication system, said non-emergency communication system configured to enable the patient to communicate with third parties and receive information regarding medical needs.

BRIEF DESCRIPTION OF THE DRAWINGS

The present subject matter will now be described in detail with reference to the drawings, which are provided as illustrative examples of the subject matter so as to enable those skilled in the art to practice the subject matter. Notably, the FIG.s and examples are not meant to limit the scope of the present subject matter to a single embodiment, but other embodiments are possible by way of interchange of some or all of the described or illustrated elements and, further, wherein:

The drawings described herein are for illustration purposes only and are not intended to limit the scope of the present disclosure in any way. The present disclosure will become more fully understood from the detailed description and the accompanying drawings wherein:

FIG. 5A shows the display with no active alerts;
FIG. 5B shows the display with an active alert for help;
FIG. 5C shows the display with an active alert for aide;
FIG. 5D illustrates use of a search box within the display;
FIG. 5E shows the display with a pop-up box listing various functions;
FIG. 5F shows the display with a pop-up box listing various communication options;
FIG. 5G shows the display with a pop-up box used for text messaging;
FIG. 5H shows the display with a pop-up box for quick text messaging;
FIG. 5I shows the display with a pop-up box indication patient is on another call;
FIG. 5J shows the display with a pop-up box with a reminder setting function;
FIG. 5K shows the display with a patient locating function;

FIG. 7A is an example of a home screen display;

FIG. 7B is an example of a notification display;

FIG. 7C is an example of a display for a specific notification;

FIG. 7D is an example of a main menu screen display;

FIG. 8A is an example of a daily schedule display organizing tasks according to a daily schedule;

FIG. 8B is an example of a daily schedule display

FIG. 8C is an example of a task shown in daily schedule display;

FIG. 9A is an example of main mail display;

FIG. 9B is an example of an opened message;

FIG. 9C is an example of a mail display including a photo;

FIG. 10A is an example of medications list display;

FIG. 10B is an example of an opened message;

FIG. 10C is an example of an opened and/or pop-up message including a skip option;

FIG. 11A is a display listing various service options;

FIG. 11B is an example of an acknowledging message;

FIG. 11C is an example of a pending request message;

FIG. 13C shows an exemplary embodiment for an account creation page for the personal contacts communication system;

Figure 1:
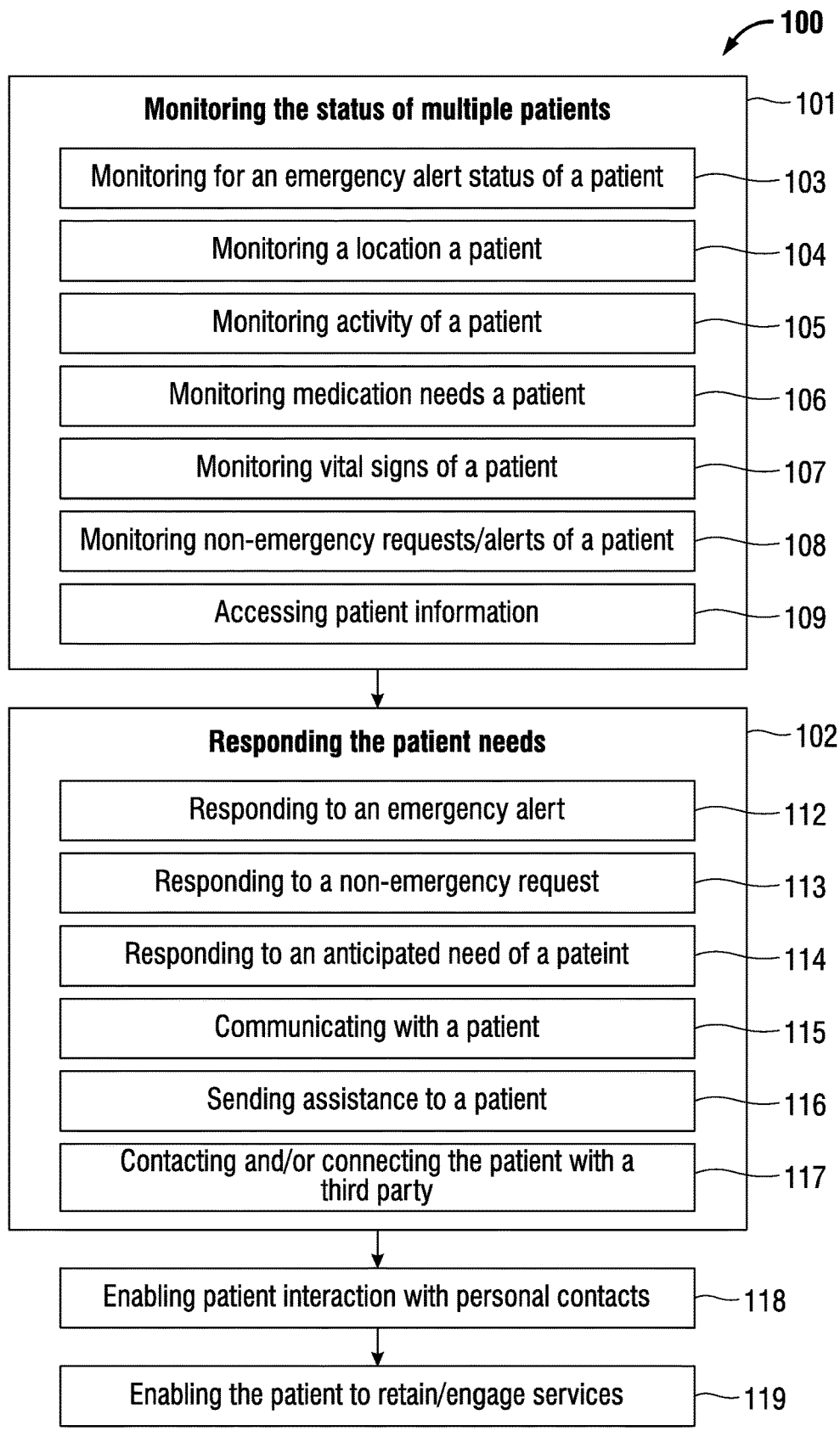
FIG. 1 shows a patient care method, according to various embodiments.

While the disclosure is subject to various modifications and alternative forms, specific embodiments thereof are shown by way of example in the drawings and the accompanying detailed description. It should be understood, however, that the drawings and detailed description are not intended to limit the disclosure to the particular embodiments. This disclosure is instead intended to cover all modifications, equivalents, and alternatives falling within the scope of the present disclosure as defined by the appended claims.

DETAILED DESCRIPTION OF ILLUSTRATIVE EMBODIMENTS

The detailed description set forth below in connection with the appended drawings may be intended as a description of exemplary embodiments in which the presently disclosed process can be practiced. The term "exemplary" used throughout this description means "serving as an example, instance, or illustration," and should not necessarily be construed as preferred or advantageous over other embodiments. The detailed description includes specific details for providing a thorough understanding of the presently disclosed method and system. However, it will be apparent to those skilled in the art that the presently disclosed process may be practiced without these specific details. In some instances, well-known structures and devices are shown in block diagram form in order to avoid obscuring the concepts of the presently disclosed method and system.

In the present specification, an embodiment showing a singular component should not be considered limiting. Rather, the subject matter preferably encompasses other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present subject matter encompasses present and future known equivalents to the known components referred to herein by way of illustration. Although the device(s) here disclosed have been described in detail herein with reference to the illustrative embodiments, it should be understood that the description may be by way of example only and may be not to be construed in a limiting sense. It may be to be further understood, therefore, that numerous changes in the details of the embodiments of the disclosure will be apparent to, and may be made by, persons of ordinary skill in the art having reference to this description. It may be contemplated that all such changes and additional embodiments are within the spirit and true scope of this disclosure as claimed below.

Unless specifically stated otherwise, references to "a", "an", and/or "the" may include one or more than one and that reference to an item in the singular may also include the item in the plural. It is to be understood that the phrases "one or more" and "at least one" refer, for example, to instances in which one of the subsequently described circumstances occurs, and to instances in which more than one of the subsequently described circumstances occurs.

The term "optional" or "optionally" refer, for example, to instances in which subsequently described circumstances may or may not occur, and include instances in which the circumstance occurs and instances in which the circumstanced do not occur. The term "about" used in connection with a quantity is inclusive of the stated value and has the meaning dictated by the context (for example, it includes at least the degree of error associated with the measurement of the particular quantity). When used in the context of a range, the term "about" should also be considered as disclosing the range defined by the absolute values of the two endpoints. For example, the range "from about 2 to about 4" also discloses the range "from 2 to 4".

The detailed description of exemplary embodiments herein makes reference to the accompanying drawings, which show exemplary embodiments by way of illustration and its best mode, and not of limitation. While these exemplary embodiments are described in sufficient detail to enable those skilled in the art to practice the invention, it should be understood that other embodiments may be realized and that logical changes may be made without departing from the spirit and scope of the invention. For example, the steps recited in any of the method or process descriptions may be executed in any order and are not necessarily limited to the order presented. Moreover, many of the functions or steps may be outsourced to or performed by one or more third parties. Furthermore, any reference to singular includes plural embodiments, and any reference to more than one component or step may include a singular embodiment or step.

Methods and systems of the present disclosure address here the need for improved and cost effective care for patients, including seniors and/or individuals of diminished capacity. In many cases, providing proper care for such individuals may be challenging and financially burdensome. Additionally, providing live-in care for senior, or residence in a retirement facility may be undesirable and invasive for both seniors and their families.

As such there is a need for a method and system which may minimize the need for live-in help, provide efficient and effective response to emergency and non-emergency situations, and/or generally enhance a patient's quality of life.

Additionally, or alternately, there is a need for an improved patient care method including a method capable of monitoring the status of multiple patients and responding to those needs.

Additionally, or alternately, there is a need for an improved patient care method including a method capable of indicating emerging and/or pending needs of multiple patients as they arise in real time, and efficiently responding to such needs.

Additionally, or alternately, there is a need for an emergency response device configured to establish wireless communication between a remote response agent and a user of the device upon an indication of a potential emergency.

Additionally, or alternately, there is a need for an emergency response system configured to detect a potential emergency and issue an alert.

Additionally, or alternately, there is a need for a patient care device configured to indicate a potential emergency, which can be worn by the patient.

Additionally, or alternately, there is a need for a patient care device configured to indicate a potential emergency, and which can also provide the patient with non-emergency functionality to assist in patient care.

Additionally, or alternately, there is a need for an improved patient care method including a method for monitoring a patient's bio-signs.

Additionally, or alternately, there is a need for an improved patient care method, comprising a service engagement system for efficiently providing at home care to the patient on an as needed basis.

With reference to the accompanying figures, and in accordance with various embodiments, the present disclosure is generally directed to patient care system and method, and more specifically to a system and method for providing remote emergency and non-emergency assistance to the patient, including remote monitoring of the patient. As used herein, the term "patient" may refer to individuals with diminishing dexterity and neurological physiological functionality and/or individuals receiving or in need or receiving medical treatment, incapable of living independently, or otherwise desire assistance in living. This may include an elderly person, a person with a handicap or disability, and/or physical or psychological condition that may benefit from assisted living.

Figure 2:
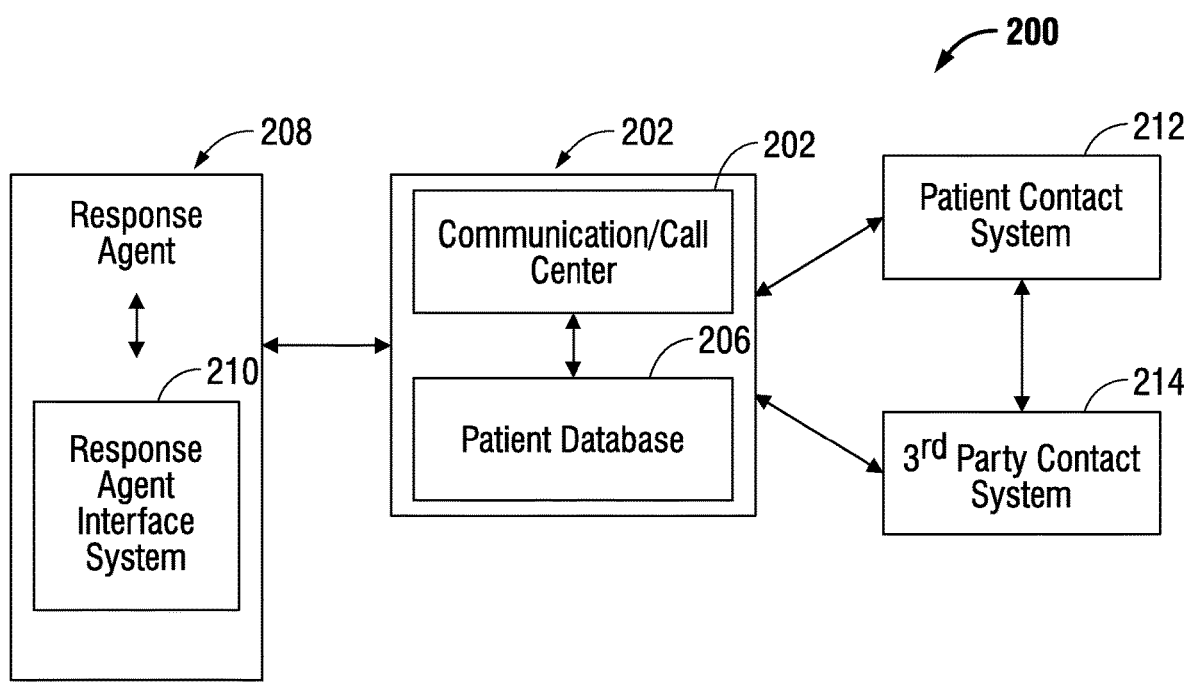
FIG. 2 is a diagram of a patient communication network according to various embodiments.

FIG. 1 shows a patient care method 100, according to various embodiments, which comprises monitoring the status of multiple patients (step 101), and responding to patient needs (step 102) by a response agent system 208 (see FIG. 2). In embodiments, each patient may be an established participant (i.e. enrolled) in the response agent system 208. In embodiments, the patient care method 100 may be implemented via a dedicated patient care device 300, configured for communication with the response agent system 208.

In embodiments, monitoring the status of multiple patients 101 may be carried out by a response agent of the response agent system 208 on an as-needed (on-call) basis, and may comprise at least one of: monitoring for an emergency alert status of a patient 103, monitoring a location a patient 104 (e.g. via GPS), monitoring activity of a patient 105, monitoring medication needs a patient 106, monitoring bio signs of a patient 107, monitoring non-emergency requests/alerts of a patient 108, accessing patient information 109, and the like. In embodiments, responding to patient needs 101 may be carried out by the response agent on an as needed basis, and may comprise at least one of: responding to an emergency alert 112, responding to a non-emergency request 113, responding to an anticipated need 114 of a patient, communicating 115 with a patient, sending assistance 116 to a patient, contacting and/or connecting the patient with a third party 117, and the like.

In further embodiments, method 100 may comprise enabling patient interaction 118 with personal contacts, such as friends and family, social groups, and the like, through the device 300. In further embodiments, method 100 may comprise enabling the patient to retain/engage 119 services of various professionals, through the device 300. Such services may include, for example transportation, house keeping, grocery shopping, food delivery, and the like.

According to various embodiments, each of said multiple patients may enroll into the response agent system 208. Additionally, each patient may reside in a private residence and/or a care facility. Accordingly, in some embodiments, the patient care method 100 may enable seniors to remain living at their residence rather than having to move into a senior care facility and/or hire a live-in caretaker. In other embodiments, the patient care method 100 may be implemented within a care facility to improve and/or optimize quality and efficiency of care within the facility. Thus, patient care method 100 provides a centralized system designed to take care of each patient's needs via consistent monitoring and/or direct communication enablement to a centralized agent.

FIG. 2 is a diagram of a patient communication network 200 according to various embodiments, for establishing communication between the patient(s) and response agent system 208, and among multiple response agents of the response agent system 208 in order to carry out the patient care method 100. In embodiments, the patient communication network may utilize various communication platforms such as Internet, intranet, cloud, broadcasting systems, etc.)

In embodiments, the patient communication network 200 may comprise a patient access center 202 including a communication/call center 204 and a patient database 206. In embodiments, the response agent system 208, through which a response agent may monitor the status of multiple patients and respond to patient needs, may be configured to operate through a response agent interface 210. In embodiments, the patient communication network 200 may further comprise a patient contact system 212, configured for enabled communication with the response agent system 208. In embodiments, the patient contact system 212 may include and/or be configured to operate through the patient care device 300. In embodiments, the patient communication network 200 may further comprise a $3^{rd}$ party contact system 214, configured for communication with the patient contact system 212 and/or response agent system 208. In embodiments, the $3^{rd}$ party contact system 214 may include an assistive service system 318, a professional service engagement system, and/or a personal contacts ("friends and family") communication system 320 (see FIG. 6). In embodiments, the response agent system 208 and the patient contact system 212 may be configured for communication via the patient access center 202 and/or communication center 204. However, this need not be the case, as in some embodiments, the patient contact system 212 and/or patient care device 300, may be configured for direct communication with the response agent system 208.

In further embodiments, the $3^{rd}$ party contact system 214 may also be configured for communication with the response agent system 208 via the patient access center 202 and/or communication center 204. However, this need not be the case, as in some embodiments, the $3^{rd}$ party contact system 214 may also be configured for direct communication with the response agent system 208.

In embodiments, the patient communication network 200 may be configured to provide stand by support to multiple patents who are enrollees of the method 100. Thus, the patient access center 202 in combination with the response agent interface 210 and patient contact system 212 and/or patient care device 300 provides a centralized network which enables the efficient constant monitoring of each patient enrolled in the system.

Response Agent System

Figure 3:
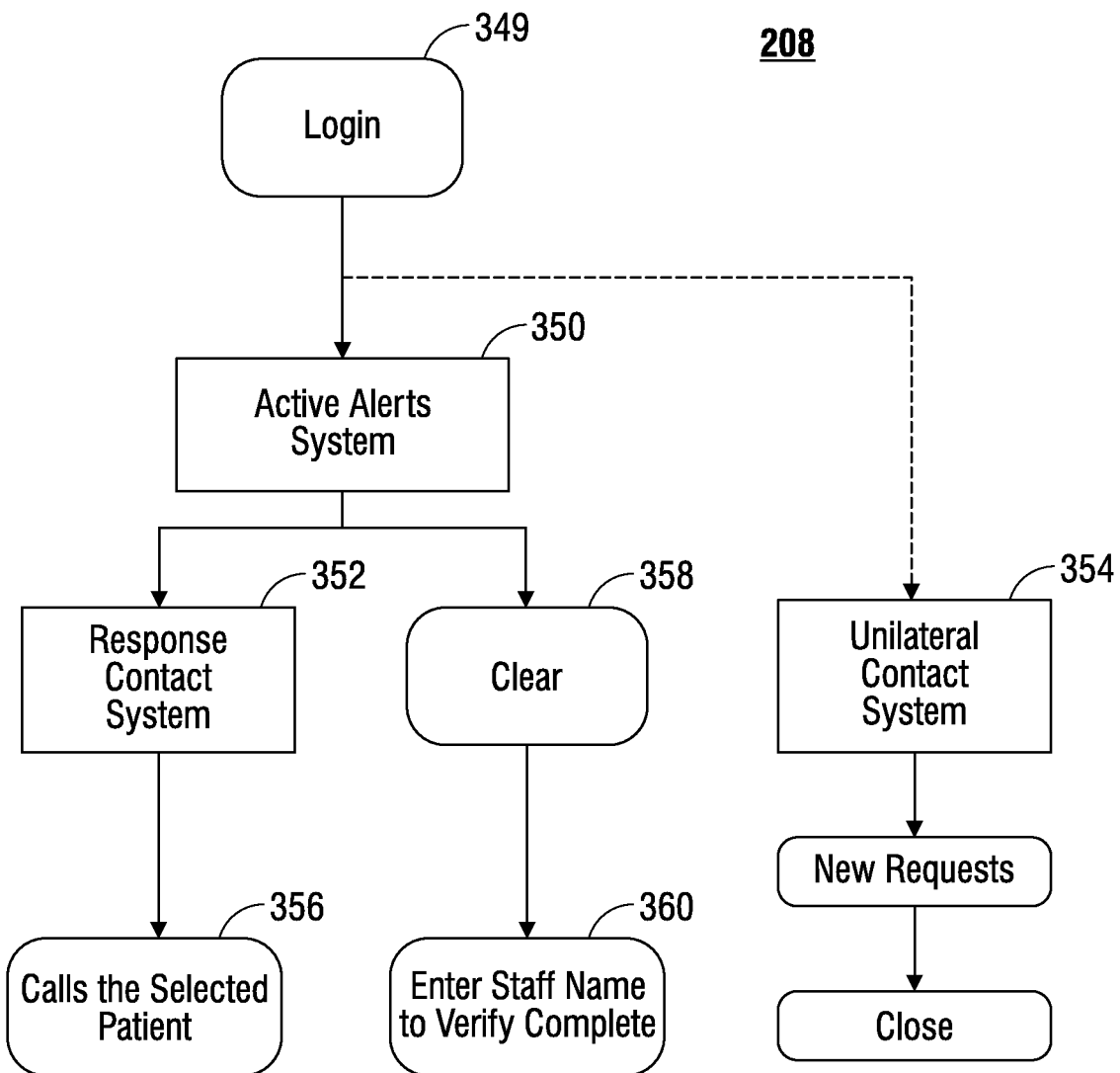
FIG. 3 is a diagram illustrating a response agent system, according to various embodiments.

FIG. 3 is a diagram illustrating the response agent system 208, according to various embodiments. In some embodiments, the response agent system may operate through a response agent interface system 210 (see FIG. 4), which may be accessed by multiple response agents via a communications network, through various device(s) (e.g. computer, phone, tablet, etc.). In embodiments, the response agent system 208 operating through the response agent interface system 210 may enable a response agent to view the status of multiple patients, and to communicate with at least one patient based on indicated and/or anticipated needs of the patient. In embodiments, a staff of multiple response agents may monitor the status of multiple patients through the response agent interface 210, such that any one of the response agents may immediately respond to an arising need of an individual patient as it appears on the response agent interface 210. In embodiments, the response agent system 208 may comprise a log in system 349 for allowing response agent access to interface system 210. Accordingly, each of the multiple response agents may be located in a common facility and/or remote from one another (e.g. at home, a private office, and the like).

In embodiments, the response agent system 208 may comprise an active alerts system 350 configured to allow the response agent to view and respond to active alerts of patients through the response agent interface 210. The active alerts may comprise, emergency alerts and/or non-emergency alerts. In embodiments, emergency alerts and/or non-emergency alerts (i.e. patient requests) may be initialed by the patient through the patient device 300. In some embodiments, emergency alerts may be automatically signaled from the patient device 300 to the response agent interface 210 in response to an indication of possible patient distress and/or danger. This may be, for example, an indication by at least one sensor, which may be incorporated within the device 300 and/or in communication with the device 300. Such sensor may include, for example, a fall sensor, a position tracking device (e.g. GPS unit), a bio monitor device, and the like. In some embodiments, non-emergency alerts (e.g. requests for assistance) may be automatically signaled by the response agent system and/or through the response agent interface 210. For example, alerts that a patient needs help with various scheduled events, such as taking medications, medical treatments, meals, etc., may be automatically indicated as non-emergency alerts.

In embodiments, the response agent system 208 may further comprise a response contact system 352, enabling the response agent to establish communication with a patient (e.g. call the selected patient 356) in response to an indication of an active alert of the patient by the active alerts system 350. In embodiments, the response agent may clear 358 an active alert from the active alerts system 350, once the response agent determines that a sufficient response has been rendered. In some embodiments, the response agent may further be required to enter his/her name or ID 360 and/or a passcode for verification and assurance to other response agents that an alert is no longer active.

In some embodiments, the response agent system 208 may further comprise a unilateral monitoring/contact system 354 for enabling the response agent to unilaterally establish communication with the patient, set and/or set reminders (e.g. push notifications) for the patient, and/or perform other proactive functions in caring for the patient. For example, a response agent may send and/or set notifications to the patient (e.g. reminders to take medications, reminders of appointments and activities, notification of visitors, etc.)

In embodiments, communication through response contact system 352 and/or unilateral monitoring/contact system 354 may comprise voice, video, and/or text communication. Additionally, communication may be may be established through the response agent interface system 210, but this need not necessarily be the case, as communication may be established through various devices and systems independent of interface system 210, which are or may become apparent with emerging technology.

Figure 4:
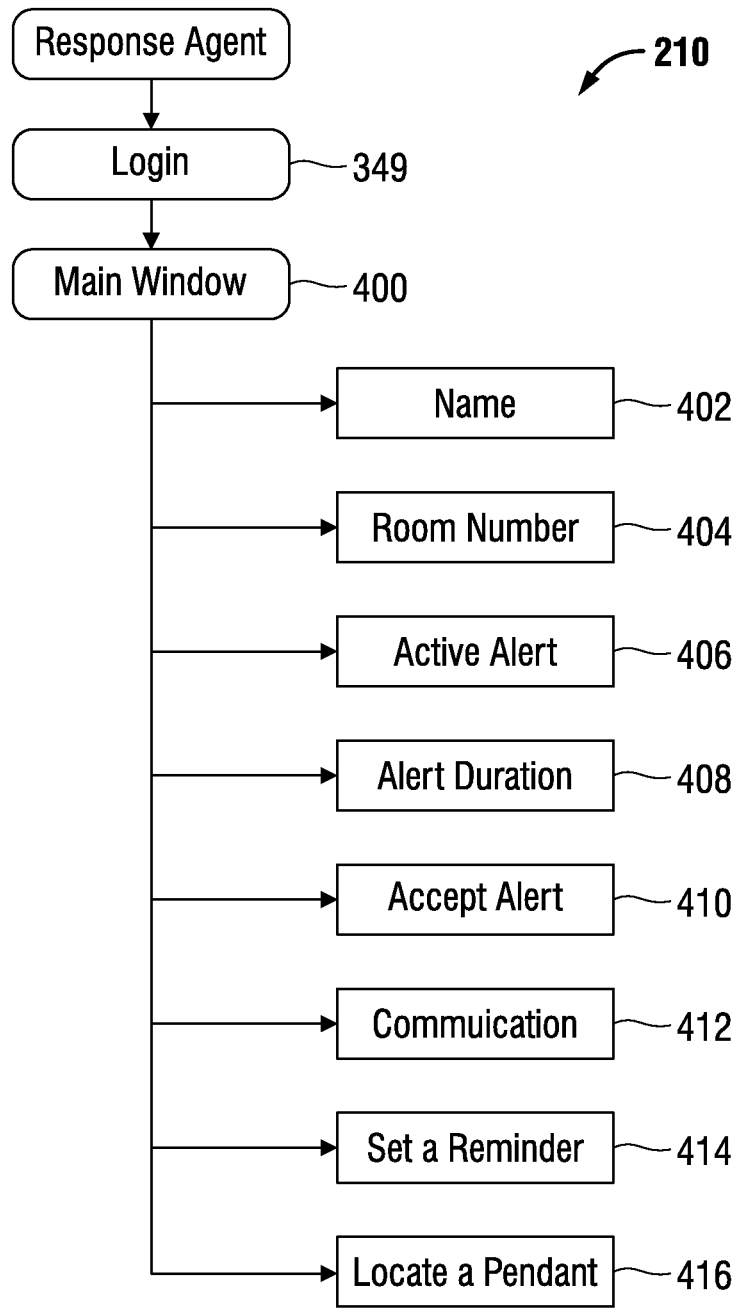
FIG. 4 is a diagram illustrating the response agent interface system, according to various embodiments.

FIG. 4 is a diagram illustrating a response agent interface system 210, according to one embodiment, for enabling at least one response agent to monitor the status of multiple patients enrolled in the response agent system 208. In embodiments, the interface system 210 may comprise at least one interactive display 400. In embodiments, the display 400 may be accessed via communication network 200 and may further include a login system 349 (which may also include a sign up system) by the response agent. In further embodiments, the display 400 may show various information items regarding at least one patient. In further embodiments, the display 400 may enable various response agent functions relating to the patient(s).

Information relating to the patient may comprise, for example, the patient's name 402; location (e.g. room number) of the patient 404; active alert status of the patient 406 (i.e. whether or not there is a pending active alert); information regarding an alert 408 which may include, for example, duration of an alert (i.e. how long the alert has been pending), nature of the alert (i.e. emergency, non-emergency, etc.), information regarding previous alerts by the patient, etc.; and the like. In some embodiments, an alert and/or it's nature may be indicated by sound and or visual effects such as a flashing red "Help" signal for an emergency alert, or the like.

According to various embodiments, the display 400 may further enable various response agent functions. In embodiments, the response agent functions may comprise acceptance of an alert 410 by any one of the staff of multiple response agents. In some embodiments acceptance of an alert 410 may serve to indicate to other response agents that an alert is being tended to, thus enabling the staff of multiple response agents to efficiently coordinate their efforts (making sure that every need is answered as quickly as possible by an available agent on standby or "on call", versus having a dedicated assistant for each patient which is not cost effective, or one assistant for multiple patients which may cause delay in assisting patients when needs arise). In further embodiments, acceptance of an alert 410 may serve to enable the accepting response agent to access information regarding the patient. Such information may include, for example, medical history/conditions, information regarding past alerts and/or emergencies, contact information for other persons who may need to be contacted and/or who may provide helpful information or assistance to the patient, etc.

In embodiments, response agent functions enabled by the display 400 may include establishing communication with a patient 412 through response agent interface system 210. In some embodiments, establishing communication 412 may be in response to an alert, and may be enabled following acceptance of an alert 410 by the response agent. In other embodiments, establishing communication 412 may be initiated by the response agent, not as a response to an alert. For example, a response agent may set a reminder for the patient, inform a patient of a call or visit by friends or family, check in on the patient, engage the patient socially, and/or invite the patient to an activity, etc., according to various embodiments. Additionally, establishing communication 412 may comprise establishing audio, visual, and/or text messaging communication, according to various embodiments.

In further embodiments, response agent functions enabled by the display 400 may comprise enabling the response agent to send and/or set a reminder 414 for a selected patient. For example, a reminder may be send and/or set as a one time or as a periodic reminder for a doctors appointment, social event(s), medication/vitamin schedule, etc.

In further embodiments, response agent functions enabled by the display 400 may comprise locating a patient 416. This may entail using a tracking device, which may be integrated with patient device 300, according to various embodiments and/or independent from the device 300.

In further embodiments, other information items and/or response agent functions relating to the patient, which may be shown or enabled on display 400 may comprise, for example, monitoring bio signs of a patient not in emergency status, accessing patient medical history, accessing contact information and/or contacting personal contacts of the patient, such as friends and family, sending the patient reading material, etc., as may be apparent to one skilled in the art.

It is noted that while response agent system may operate through a response agent interface system display 400 which is commonly accessible by the response agent, the response agent system may also be configured to operate via dissemination or broadcasting of alerts to response agents, which may appear (e.g. as push notifications, pop-ups, etc.) on each agent's individual device (e.g. cell phone, computer, or other designated instrument etc.). In some embodiments, a response agent receiving such an alert may indicate an acceptance of a response duty, which may be conveyed to other agents. In some embodiments, such alerts may be conveyed to response agents within a vicinity or radius from where the alert originates. In some embodiments, the alerts may be emergency alerts. In some embodiments, a system for broadcasting alerts may be implemented in conjunction with the response agent interface system display.

Example of Display for Response Agent Interface System

FIGS. 5A-K are examples of a display 400, which may be a "home screen" 501 through which response agent interface system 210 may operate. As shown in the figures, the display 400 may comprise various information items and/or interactive elements, including response agent function-control buttons on one or more display windows. Additionally, the display 400 may utilize various pop-ups, navigation links, and the like, according to various embodiments.

Figure 5A:
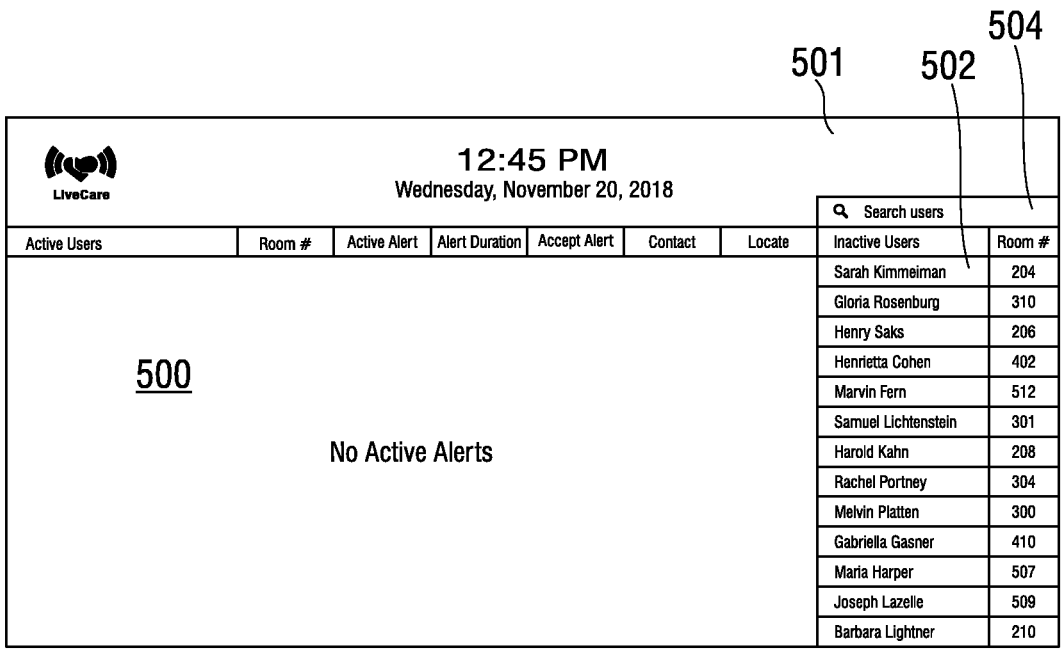
FIGS. 5A-K show examples of a display 400, for the response agent interface system, according to various embodiments.

In one embodiment, the display may comprise an "active alerts" section 500, listing any patients with active alerts. In further embodiments, the display 400 may include an "inactive patient" section 502, which may list patients enrolled in the system. In some embodiments, the display 400 may comprise an active alerts section 500 on a central section of the display, and an inactive patient section 502 on a margin of the display 400. As shown in FIG. 5A, when there are no active alerts, the active alerts section 500 may appear blank.

Active Alerts

Figure 5B:
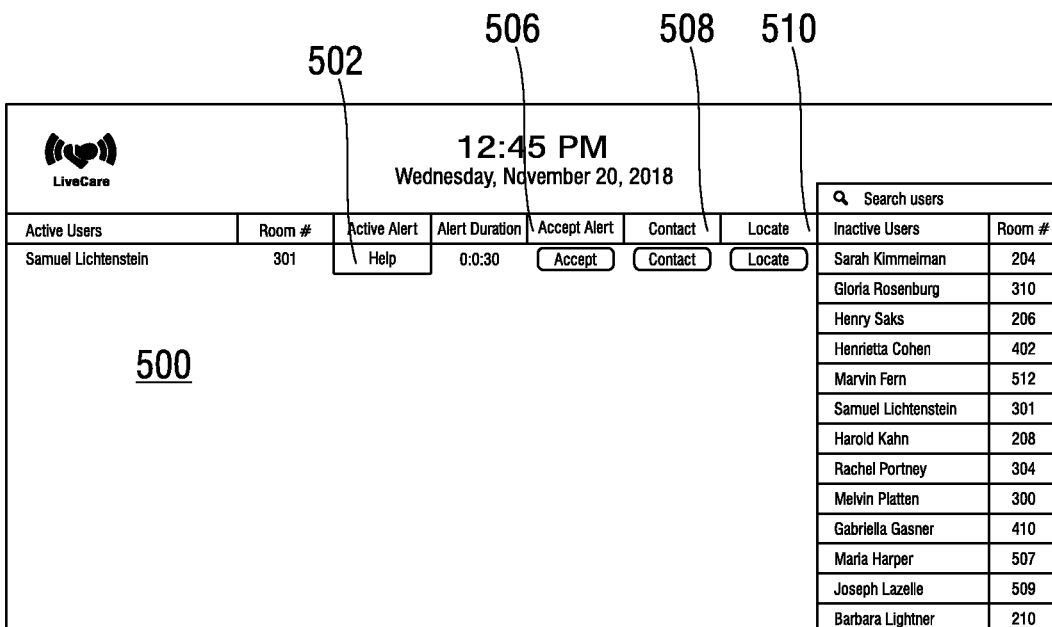

As shown in FIG. 5B, when an alert is initiated, an active alert status 406 may be indicated and accompanied by information regarding the subject patient. Additionally, response agent function-control icons/buttons may appear in the active alerts section 500 accompanying the active alert. For example, as shown in FIG. 5B, information regarding the subject patient may include the patient's name 402, location 404 (e.g. room number), and information regarding the alert 408, such as "alert duration", according to various embodiments. Additionally, response agent function-control buttons may include, for example, an alert acceptance button 506, on which the response agent may click to indicate acceptance of the alert 410; a "contact" button 508, on which the response agent may click to establish communication with the patient 412; and a "locate" button 510 on which the response agent may click for locating patient via a position tracking device. In some embodiments, a response agent may be required to accept the alert to access further function buttons and/or information. In some embodiments, the patient's name may be removed from the active alerts section 500 once an alert is accepted and/or once a response agent otherwise indicates that the patient's needs have been tended to. Other information regarding the patient in need and/or other response agent function buttons may also appear in the active alerts section 500, such as a friends and family contact button, friends and family contact information, information regarding a previous alert by the patient, medical conditions information, function buttons for accessing various information, etc. according to various embodiments.

Figure 5C:

In further embodiments, various graphical elements may accompany an alert. Such graphical elements may serve to indicate the type of alert (e.g. emergency or type of non-emergency; see FIGS. 5B and C). For example, a graphic element such as a red "Help" signal 512 designed to draw attention, may accompany an emergency alert indication, as shown in FIG. 5B. Other attention drawing elements, including sound, animation (e.g. flashing) may accompany the emergency alert indication as well, according to various embodiments. For a non-emergency alert, an indication such as an "Aide" 514, "maintenance", etc., for example, may appear, and may be distinguished by a different color, design, etc. as shown in FIG. 5C.

Inactive Patient Care

Figure 5D:
Figure 5E:
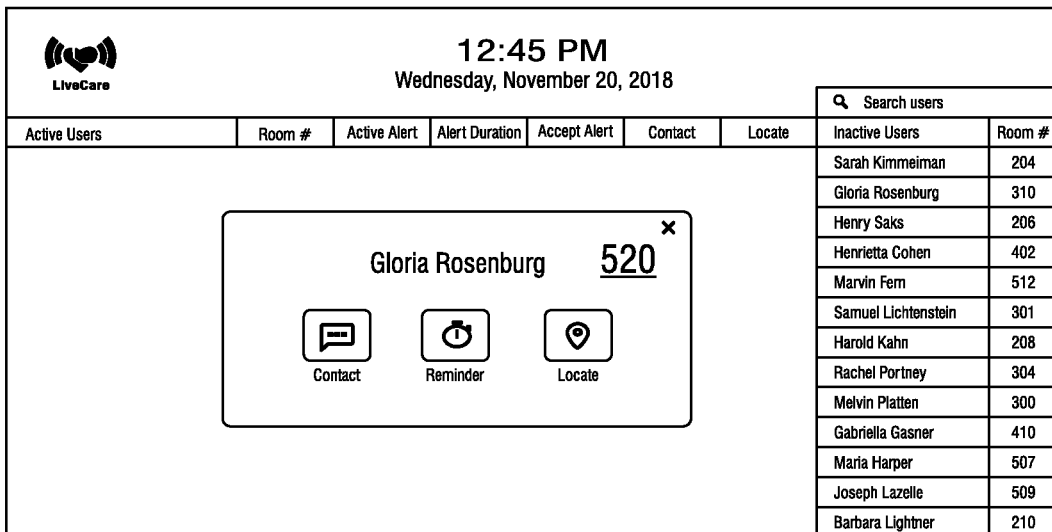

In embodiments, the inactive patient section 502 may allow a response agent to search for a patient by name (e.g. by scrolling down the patient list and/or typing in a name and/or initial characters of a name in a search box 504, as shown in FIG. 5D). In some embodiments the inactive patient section 502 may include other information, such as location 404 of the patient (e.g. room number), contact information for the patient and/or personal contacts, age of the patient, medical condition, etc. In the example shown, a room number is listed for each patient, as the example depicts a system 210 used for patients residing in a common facility. However, in embodiments where patients may not reside in a common facility, other location information, if used, may be listed.

Additionally, the search agent may select a patient and may further carry out various functions with respect to the selected patient, such as establishing communication with the patient 412, send and/or set a reminder 414 for the patient, locating a patient 416, etc., according to various embodiments.

Examples of Response Agent Functions

In embodiments, upon indicating acceptance of an alert for a patient in the active alerts section 500 or upon selection of a patient from the inactive patient section 502 (e.g. by clicking, hovering over, right clicking, etc. the patient's name) a response agent may carry out various functions with respect to the selected patient. In some embodiments, the response agent may click on a function tab, such as "contact" 508, "locate" 510, etc. In some embodiments, a "pop-up" item 520 (box) listing various functions may appear upon selection of a patient (see FIG. 5E). Preferably, such pop-up box appears on a lower section of the screen so as not to block any active alerts that may appear in the active alerts section 500. Thus, the pop-up box allows for various functions to be unobtrusively enabled on a screen.

In the examples shown in the figures, "locate" and "contact" function tabs appear in the active patients section 500, but the inactive patients section 502 uses the pop-up item 520 (which also lists an option for sending/setting a reminder 414). However, this need not necessarily be the case, as either section 500 or 502 may utilize pop-up boxes, function tabs, and other elements, or combinations thereof, according to various embodiments. FIGS. 5F-K illustrate further examples of pop-up elements for carrying out various functions by the response agent.

Figure 5F:
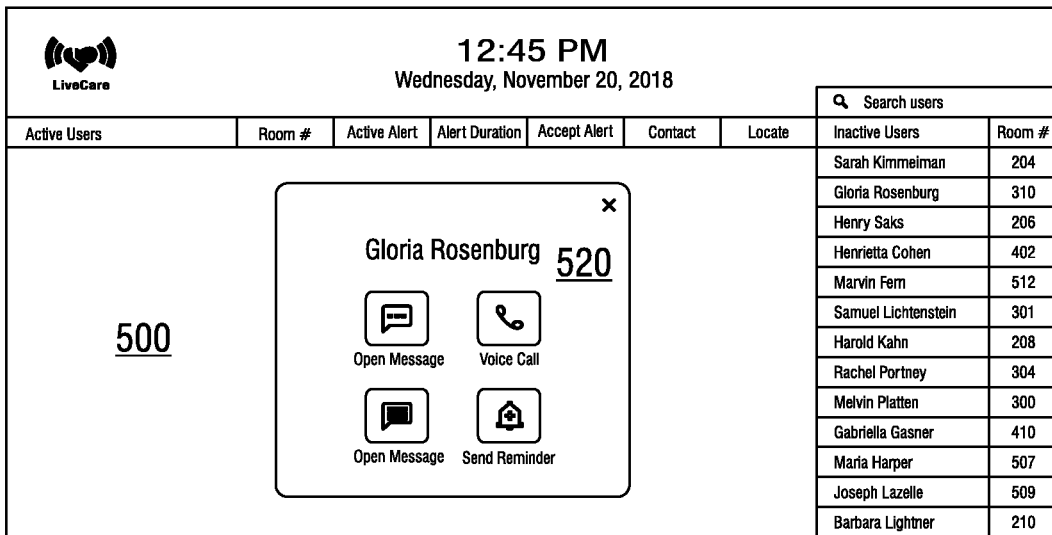
Figure 5G:
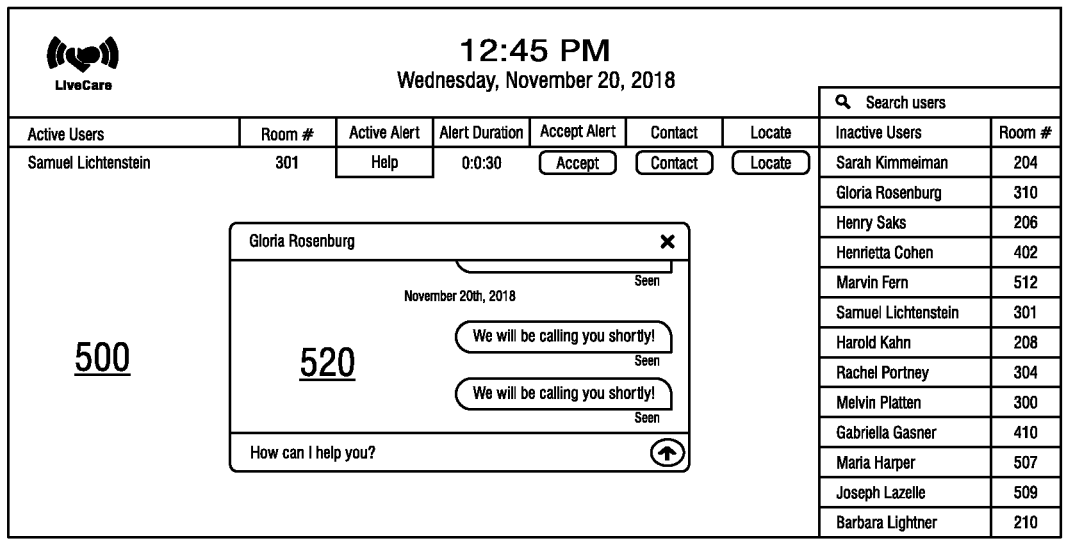
Figure 5H:
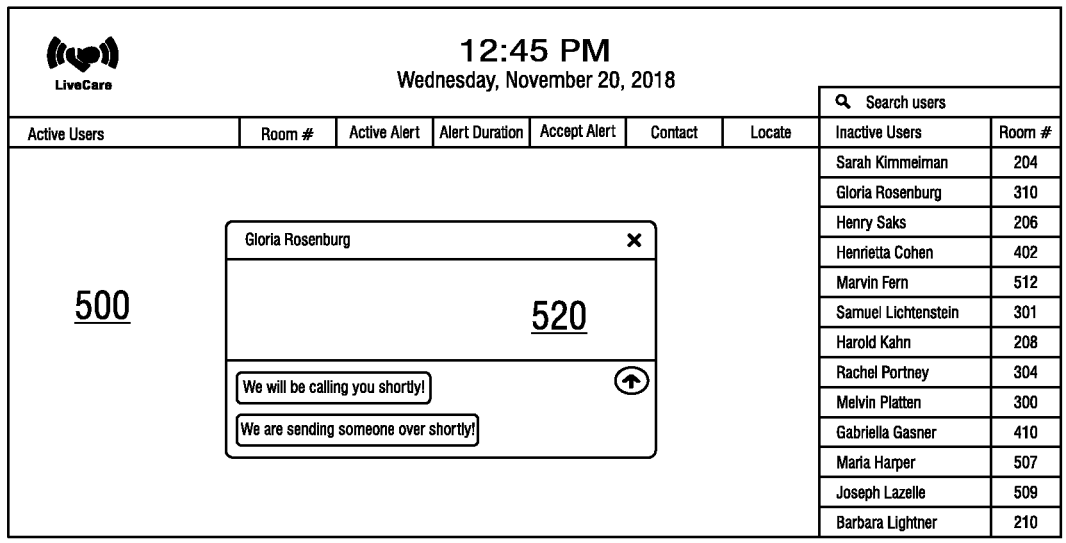
Figure 5I:
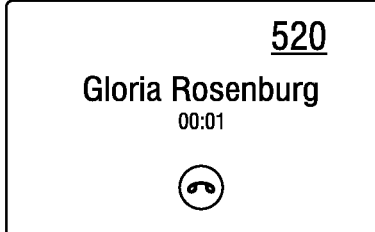

FIGS. 5F-5H show examples of communication functions which may be carried out on display 400. In one example, as shown in FIG. 5F, pop-up item 520 may provide various options for establishing communication with the patient 412, such as voice and/or video call, text messaging (i.e. starting a text message dialogue, as illustrated in FIG. 5G), and/or quick text (i.e. selecting a text message from pre-scripted options for a quick response, as shown in FIG. 5H). According to some embodiments, a text messaging dialogue may show messages exchanged in a previous text messaging dialogue, and may further indicate that a message has been opened and/or seen by the patient. In further embodiments, the pop-up box 520 may indicate if the selected patient is on another call or otherwise unavailable (see FIG. 5I). In further embodiments, the response agent may establish a voice and/or visual communication with the patient via display 400.

Figure 5J:
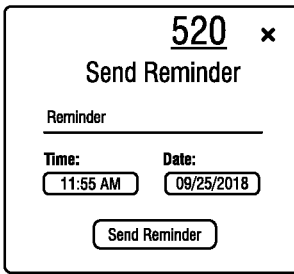

FIG. 5J shows an example of a reminder setting function, which may be carried out by the response agent. In the example shown, the pop-up item 520 may appear, prompting the response agent to fill out various information items, such as the reminder message, date, time, etc.

Figure 5K:
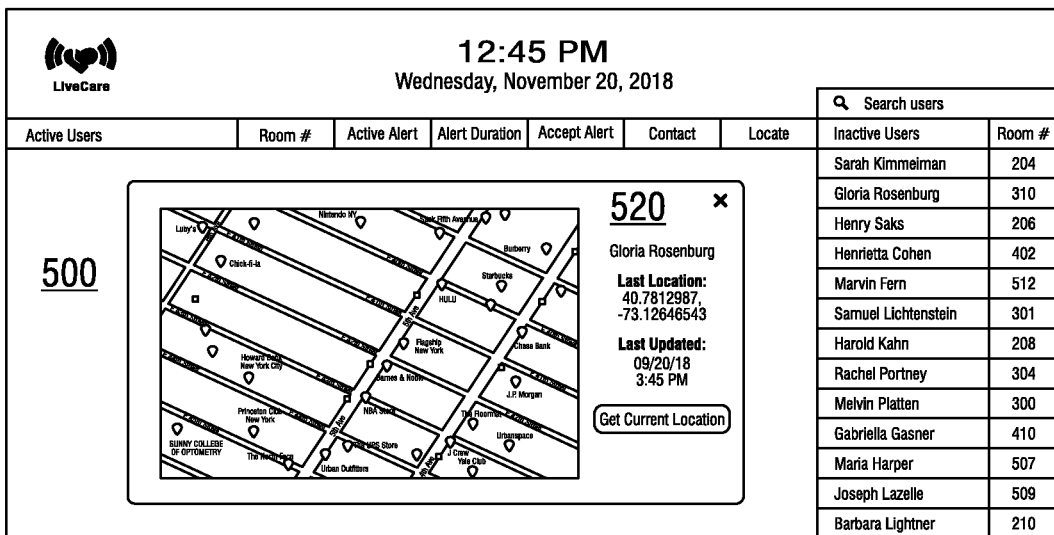

FIG. 5K shows an example of a patient locating function which may be carried out by the response agent to locate a patient via a tracking device worn or carried by the patient. This may be a tracking device embedded in the patient care device 300. According to various embodiments, upon clicking on a locate function, a location map 524 may appear showing the patient's whereabouts.

Patient Contact System

Figure 6:
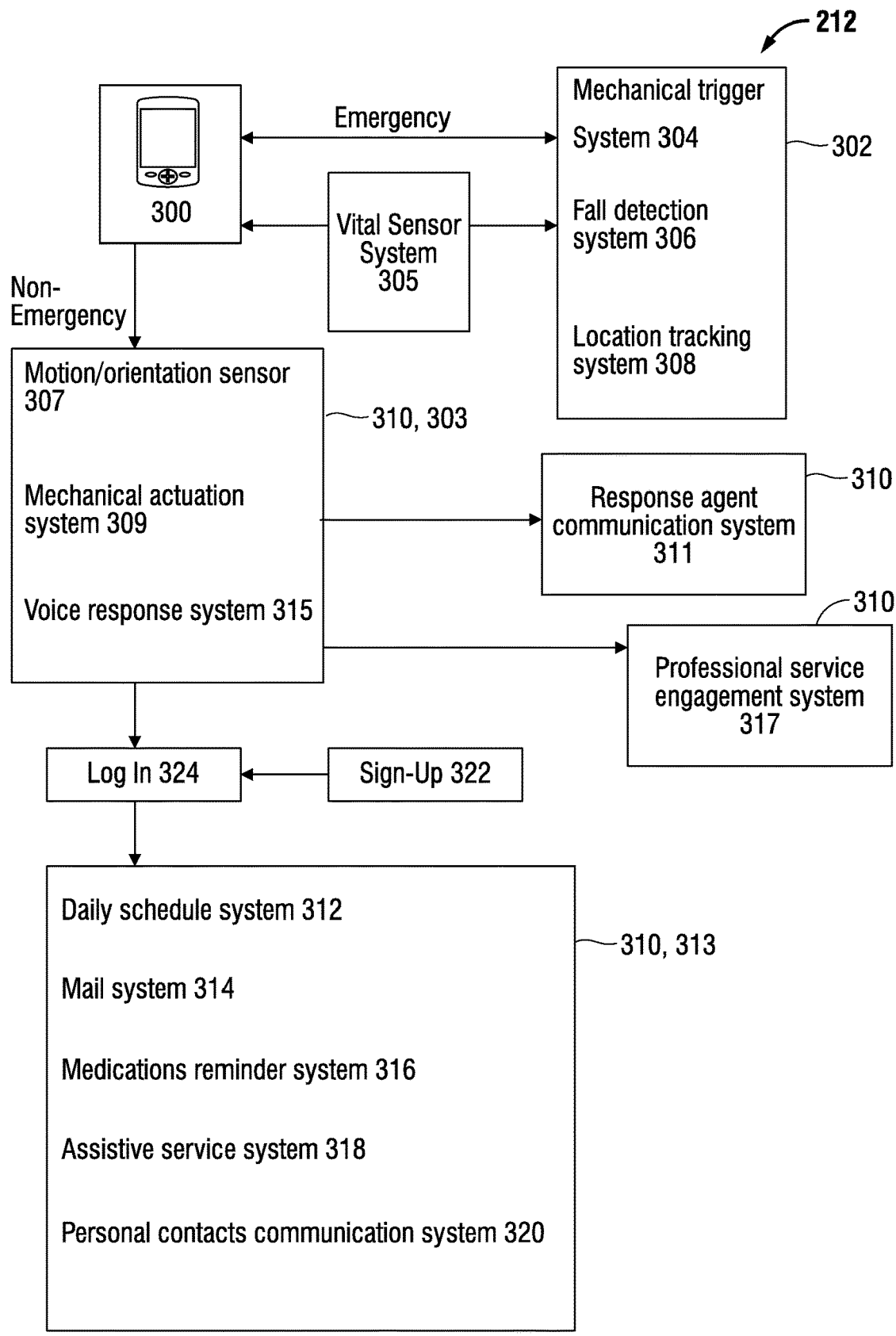
FIG. 6 is a diagram illustrating a patient contact system, according to various embodiments.

According to various embodiments, as shown in FIG. 6, the patient contact system 212 implemented through patient care device 300 may comprise an emergency activation system 302 configured to send an emergency alert to the response agent system 208. In further embodiments, the patient contact system 212 may comprise a non-emergency function system 310, designed to assist the patient in managing daily activities. According to various embodiments, the non-emergency function system 310 may include a non-emergency activation system 303, and/or a non-emergency patient utility system 313, as described below. In further embodiments, the non-emergency function system 310 may comprise a non-emergency response agent communication system 311 and/or a professional service engagement system 317. In embodiments, non-emergency response agent communication system 311 and/or a professional service engagement system 317 may be part of the non-emergency patient utility system 313

Emergency Activation System

According to various embodiments, the emergency activation system 302 may comprise at least one emergency trigger. In embodiments, the emergency trigger may comprise an emergency mechanical trigger system 304, such as a "help" button, which can be mechanically/physically activated (e.g. pressed, flipped, turned, switched etc.) by the patient to send an emergency alert. (It is noted, the term button, as used herein may refer to a physically moveable element of any geometric configuration, e.g. disk, rod, bar, cube, etc.) In further embodiments, the emergency trigger may comprise a fall detection system 306, configured to send an emergency alert upon detection of a fall of a patient wearing the device 300. Other emergency triggers may include a voice distress call by the patient, distressed bio signs of a patient, indication that the patient is outside an expected location, etc. Such triggers may be actuated via responsive systems and/or elements embedded in the device 300 and/or via other devices/systems in communication with the device 300. For example, a bio sensor system 305 ("vital sensor system") as described below, may include at least one monitor, which may be worn by the patient, and configured to detect a patient's bio signs (e.g. blood pressure) then transmit the detected signal to the device 300, wherein upon detection of an abnormality, the emergency activation system 302 may send an emergency alert to the response agent system 208. In another example, a location tracking system 308 comprising a GPS may be embedded in the device 300 and configured to track the location of the device for determining when the device 300 (assumed to be with the patient) is located outside a region where the patient is expected to be. Thus, upon detection that the patient is outside expected boundary, the emergency activation system 302 may send an emergency alert to the response agent system 208.

In some embodiments, patient care device 300 may be configured to automatically open a voice and/or visual communication channel between the device 300 and response agent and/or other caretaker. For example, upon an emergency alert initiated via the patient care device (via emergency activation system 302 and/or vital sensor system 305), the device 300 may establish automatic voice and/or visual communication with the response agent, without the patient having to answer a call. In some embodiments, the response agent may call back, wherein the device 300 may automatically establish voice and/or visual communication after a predetermined number of "rings" (e.g. 1 or 2 rings). As such, voice and visual communication can be automatically enabled through the device 300, without patient activation, wherein an emergency alert may allow the responding party to automatically see and/or hear the patient, even if the patient is unable to manually handle or operate the device, according to various embodiments.

Non-Emergency Activation System

According to various embodiments, the non-emergency activation system 303 may comprise at least one non-emergency actuator, i.e. mechanism for turning on the device. For example, a non-emergency actuator may comprise a device motion and/or orientation sensor 307, which is responsive to non-emergency movement (as opposed to fall detection) and/or orientation of the device 300. Such non-emergency movement/orientation may include, for example, tilting the device, lifting the device, orienting the device to face upwards, etc. In some embodiments, the non-emergency actuator may comprise a non-emergency mechanical actuation system 309, such as a non-emergency button; a non-emergency activation motion of the emergency "help" button (i.e. of emergency mechanical trigger system 304); a touch sensor element, such as a capacitive touch sensor and/or capacitive touch screen 700 (see FIG. 7) of the device 300; etc., and combinations thereof. In some embodiments, the non-emergency trigger may comprise a voice response system 315. In embodiments, the non-emergency activation system 303 may employ various combinations of the motion and/or orientation sensor 307, mechanical actuation system 309, and/or voice response system 315 for activating the device. Additionally, a patient may control various functions of the device 300 via voice commands through the voice response system 315, and/or touch commands through the capacitive touch screen 700.

Response Agent Communication System

In embodiments, the response agent communication system 311 may allow the patient to send non-emergency alerts to the response agent system 208, through device 300, which may be requests for assistance, and the like. In embodiments, requests for assistance may include requests for maintenance (i.e. help with housekeeping chores), and may be particularly suitable for patients living in a care facility.

In embodiments, alerts sent via the agent communication system 311 may appear, for example, as non-emergency alerts in the inactive patient section 502 of the response agent interface system 210.

Additionally, the response agent communication system 311 may further allow the response agent to establish communication with patient 412, and send and/or set a reminder 414 for the patient, and the like. In some embodiments, the response agent communication system 311 may be part of the patient utility system 313 and/or require patient login, as described below.

Non-Emergency Patient Utility System

According to various embodiments, the non-emergency patient utility system 313 may incorporate various applications and/or functions to provide the patient with emotional support, assist the patient in performing daily activities, and handle physical and cognitive challenges. In embodiments, the non-emergency patient utility system is further aimed at fostering in the patient an emotional attachment to the device 300, in order to encourage the patient to carry the device, which can ultimately be a lifesaving tool.

According to various embodiments, the non-emergency patient utility system 313 may comprise, for example, a daily schedule system 312, which may list various task and/or appointment reminders for the patient. In further embodiments, the system 313 may further comprise a mail system 314 for enabling the patient to communicate with friends and family, response agent(s), and/or other caretakers. In further embodiments, the system 313 may further comprise a medications reminder system 316. In yet further embodiments, the system 313 may comprise an assistive service system 318, to enable the patient to send direct requests for non-emergency assistance and for maintenance help. In yet further embodiments, the system 313 may comprise a personal contacts communication system 320, to enable the patient to easily connect with individuals such as friends and family. In some embodiments, functions performed by systems 312, 314, 316, 318, and/or 320, may overlap.

In some embodiments, the non-emergency response agent communication system 311 and/or the professional service engagement system 317 (see FIG. 14) may be a part of the non-emergency patient utility system 313 and/or be configured to perform overlapping functions.

In some embodiments, the non-emergency patient utility system 313 may also include a sign-up system 322 and/or a login system 324, for enabling patient access to at least one of the non-emergency functions (i.e. 312, 314, 316, 318, 320, and/or 311 and/or 317) and/or for providing privacy and security control to the patient.

In some embodiments, the patient care device 300 may be customized to include certain ones, but not all of non-emergency functions (i.e. 312, 314, 316, 318, 320, and/or 311 and/or 317). In some embodiments, patient care device 300 may be customized to include other applications and/or widgets which may be downloaded onto the device 300.

Examples of Home Screen/Main Menu

FIGS. 7A-D show various examples of displays for a home screen 700 and/or a main menu 702 for the device 300. In embodiments, home screen 700 and/or main menu 702 may be used to access the Non-emergency patient utility system 313.

Figure 7A:
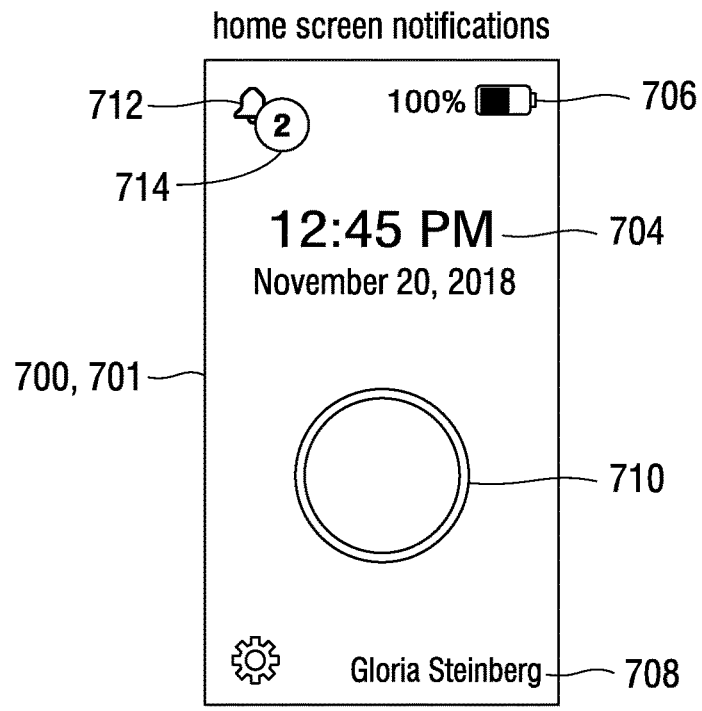
FIGS. 7A-D show various examples of displays for a home screen and/or a main menu for the patient care device, according to various embodiments.
Figure 7B:
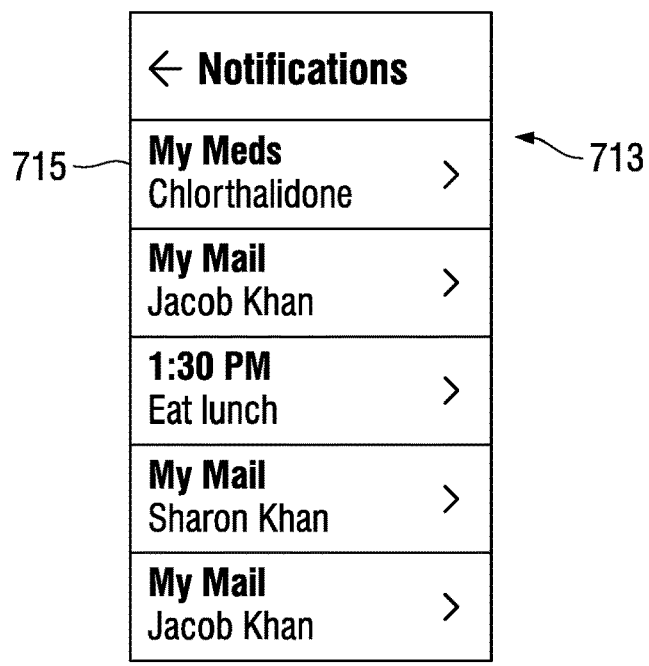
Figure 7C:
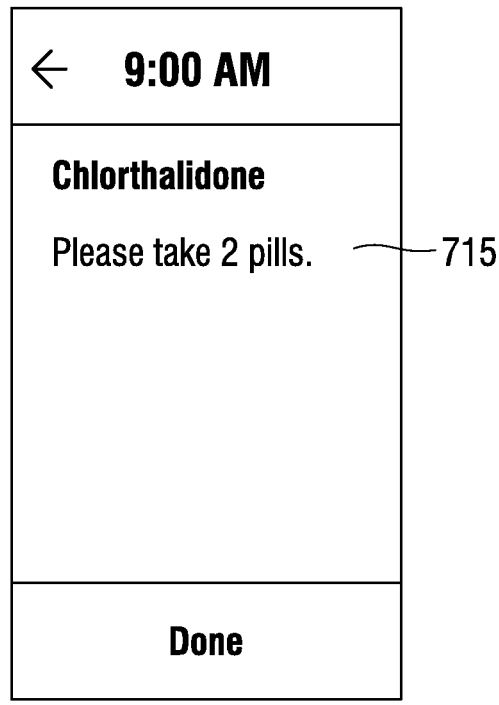

As shown in FIG. 7A, a home screen display 701 may include, for example, various items of general information, such as a time and date 704, battery level 706, patient's name 708, etc.

In embodiments, the display may comprise a virtual "unlock" button 710 on which the patient may touch/tap to unlock the device 300 and access various functions, which may be functions of the non-emergency patient utility system 313. In embodiments, such "unlock" button 710 may be, for example, a logo, or any other graphical design. In some embodiments, a password and/or biometric (e.g. fingerprint) may be required to unlock the device. In further embodiments, the home screen display 700 may include a virtual emergency activation element ("alert button").

In further embodiments, the home screen display 700 may include a notification icon 712. In some embodiments, the number of pending notifications (e.g. reminders, mail messages, etc.) may be denoted by a number 714 next to the notification icon 712, as shown. In some embodiments, the patient may access a list of pending notifications 713 by tapping on the notification icon, as exemplified in FIG. 7B. In further embodiments, the patient may tap to view a specific notification 715 from the list 713, as exemplified in FIG. 7C.

Figure 7D:
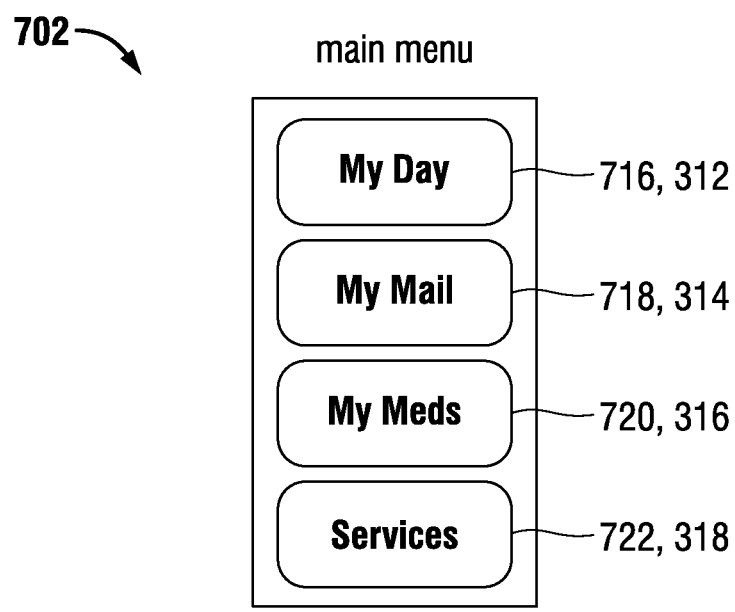

FIG. 7D shows a main menu screen display 702, which may be accessed by "unlocking" the device. In alternate embodiments, the display 702 may itself serve as the home screen. As shown in the figure, the main menu screen display 702 may include virtual function "buttons" for accessing various functions, which may be functions of the non-emergency patient utility system 313. Additionally, according to various embodiments, the display 702 may be specifically configured to provide ease of use of the device and to remind patients of important daily chores, by providing a short list of less than 10, and preferably less than about 5 or 6 items, which are prominently displayed on the screen 700. This may be particularly useful for elderly patients and/or patients suffering from cognitive disabilities.

As an example, main menu screen display 702 may include buttons prominently listing different functions, such as "My Day" 716, "My Mail" 718, "My Meds" 720, and "Services" 722, for accessing the general reminder system 312, a mail system 314, a medications reminder system 316, and an assistive services system 318, respectively, as shown in the figure. Other functions buttons may be included as well, such as the personal contacts communication system 320, the professional service engagement system 317, etc., according to various embodiments.

Example of Daily Schedule System

Figure 8A:
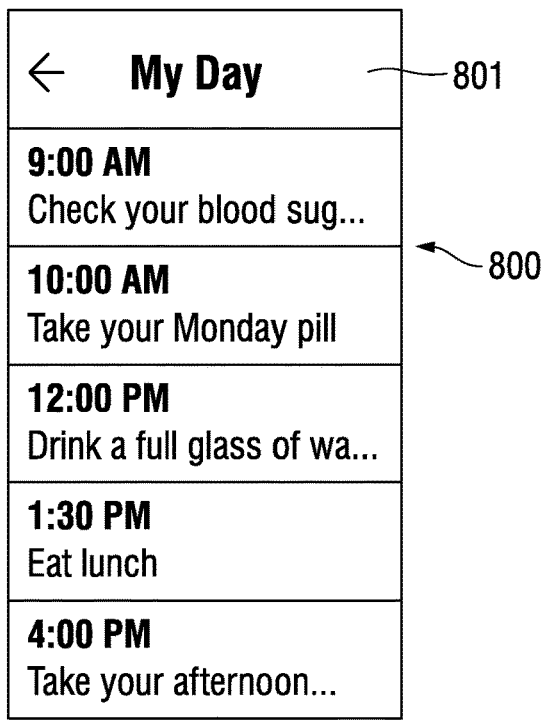
FIGS. 8A-C show various examples of displays for a daily schedule system, according to various embodiments.
Figure 8B:
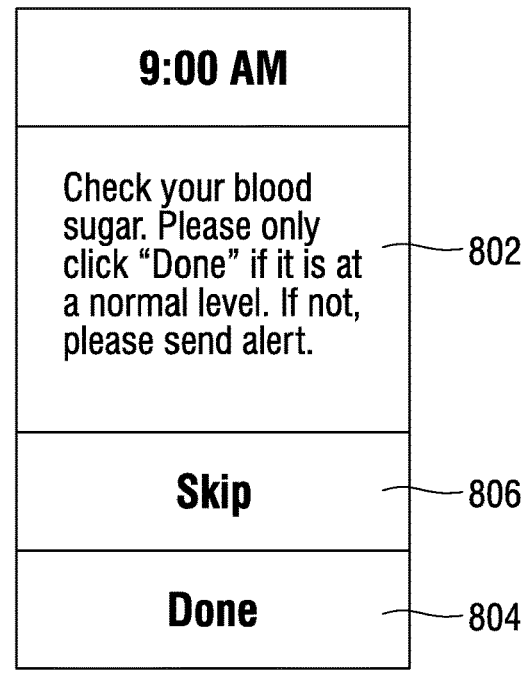
Figure 8C:
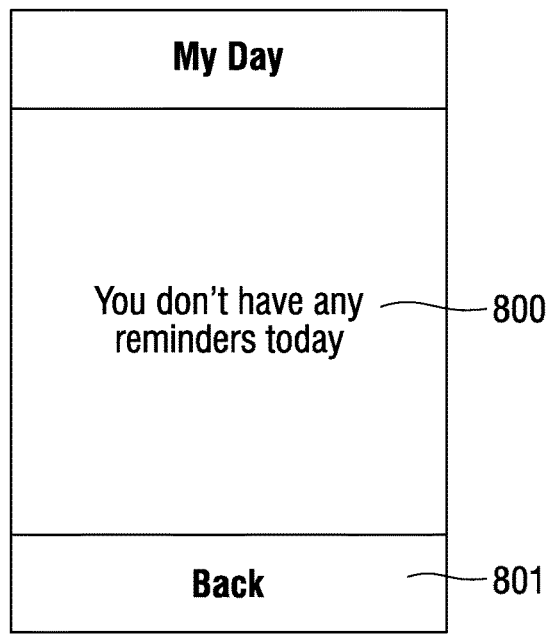

According to various embodiments the daily schedule system 312 (which may be accessed, for example, by tapping on the "My Day" button 716; see FIG. 7D) may comprise a daily schedule display 800, listing various task and/or appointment reminders for the patient, as exemplified in FIGS. 8A-C. As with display 702, display 800 may also provide a short list of prominently displayed items, for ease of use to the patient, according to various embodiments.

In embodiments, the reminders may be set by the patient. In some embodiments, daily reminders may also be set by a response agent. In further embodiments, daily reminders may also be set by other persons caring for the patient, such as family members.

According to an exemplary embodiment as illustrated in FIG. 8A, the daily schedule display 800, may organize task/reminders according to a time schedule or otherwise indicate that there are no scheduled reminders for the day (see FIG. 8C). Additionally, the schedule display 800 may include a "back" button/arrow 801 for exiting the daily schedule system 312 or schedule display 800.

In embodiments, the schedule display 800 may indicate that a task is past due (e.g. by highlighting and/or changing background color, icon indication, flashing, etc.). Additionally, a task which is currently due or past due may pop-up on the device (e.g. home screen) according to various embodiments. In some embodiments, the patient may tap on a specific listed task to open a screen 802 detailing that task (see FIG. 8B). In embodiments, the patient may indicate that he/she wishes to "skip" a task (e.g. by taping a "skip" button 806); or that the task is complete (e.g. by tapping a "Done" button 804), whereupon the specific task may be removed from the list. In some embodiments, the patient may set a later reminder for the task.

Example of Mail System

Figure 9A:
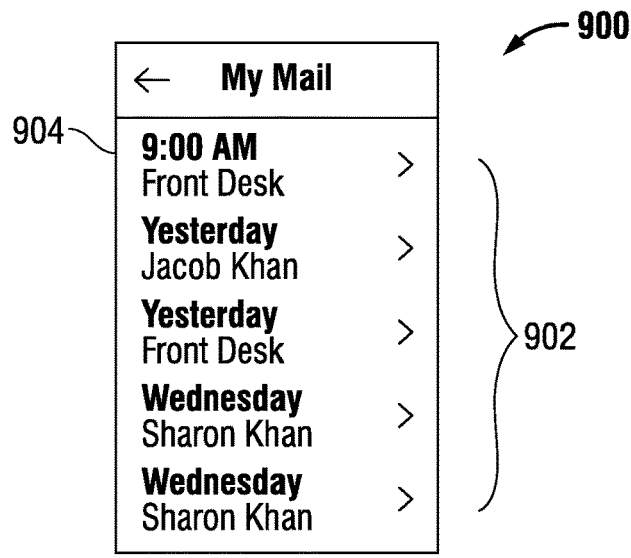
FIGS. 9A-C show various examples of displays for a mail system, according to various embodiments.
Figure 9B:
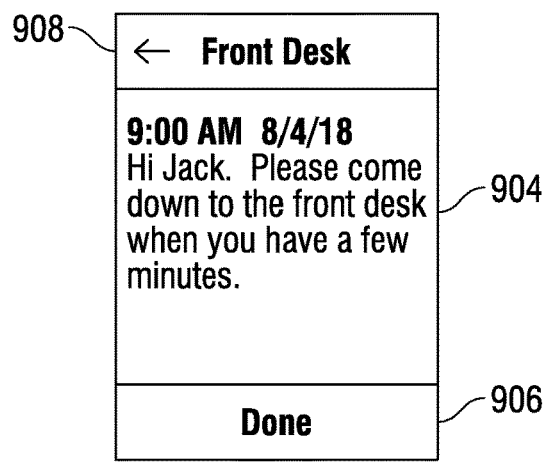
Figure 9C:
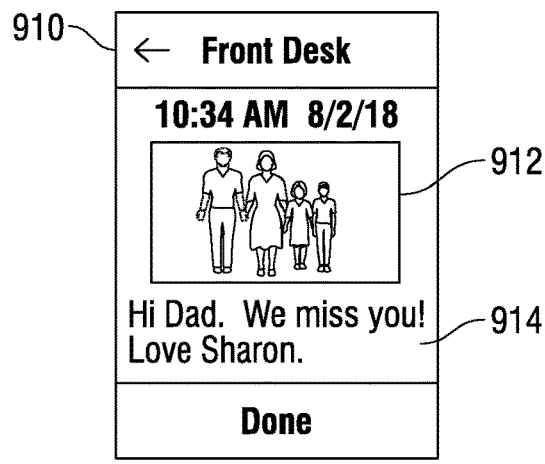

According to various embodiments the mail system 314 may enable the patient to send and receive messages, which may be from family, friends, response agent(s), other care takers, etc., as exemplified in FIGS. 9A-C.

According to an exemplary embodiment, as illustrated in FIG. 9A, the mail system 314 (which may be accessed, for example, by tapping on the "My Mail" button 718; see FIG. 7D) may include a main mail display 900 showing a list 902 of messages. In embodiments, the list of messages may be unread/unopened messages and/or messages which the patients may indicate that he/she desires to keep on the list 902. As exemplified in FIG. 9B, a patient may tap on a message 904 to open it. In embodiments, the message 904 may include an indicator button 906 (e.g. "Done") on which the patient may tap to indicate that the message may be removed from the list 902. In further embodiments, the message 904 may include a back button 908 on which the user may tap to go back to the list 902. In some embodiments, a mail message 910 may include a photo 912, as exemplified in FIG. 9C. In further embodiments, the message 910 may include an emotional interactive element 914 (e.g. "like" or heart shape, etc.) on which a user may tap to indicate sentimentalities regarding a photo and/or message (e.g. the user may tap on a heart shape to indicate that he likes a photo).

Examples of Medications Reminder System

Figure 10A:
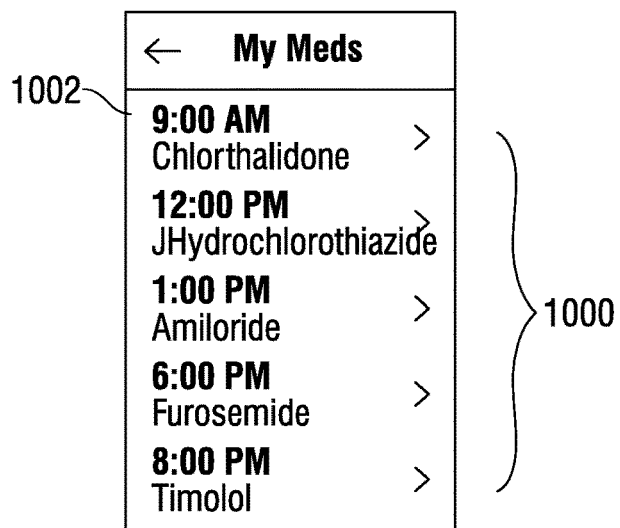
FIGS. 10A-C show various examples of displays for a medical reminder system, according to various embodiments.
Figure 10B:
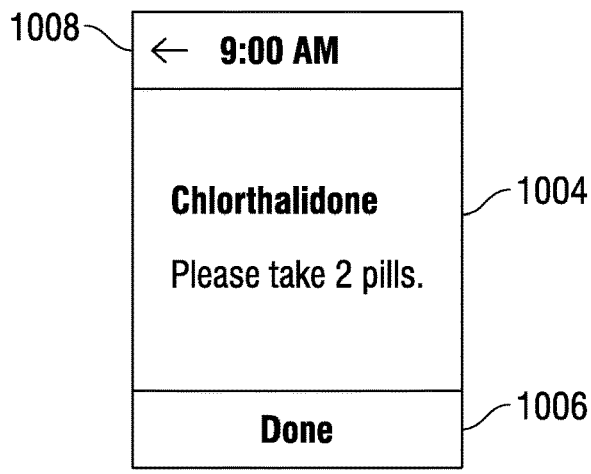
Figure 10C:
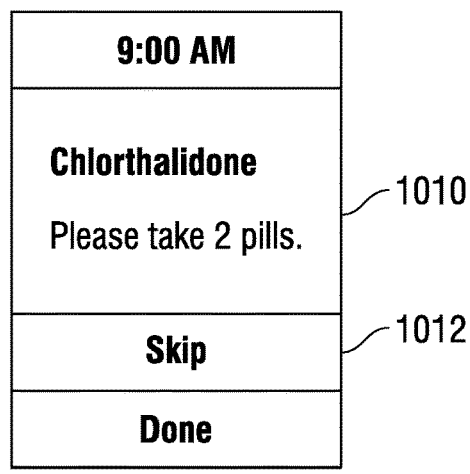

According to various embodiments the medications reminder system 316 may remind the patient of a medication schedule, as exemplified in FIGS. 10A-C.

According to an exemplary embodiment, as illustrated in FIG. 10A, the medications reminder system 316 (which may be accessed, for example, by tapping on the "My Meds" button 720; see FIG. 7D) may include a medication list display 1000 showing a list of medications that the patient needs to take, with the time to take each medication. In embodiments, the list may include an indication for any medication which is past due (e.g. by highlighting, color, flashing, etc.). In embodiments, medication reminders may be set by the patient, a response agent, and/or other caretakers such as family members, doctor(s), pharmacist(s), etc.

As exemplified in FIG. 10B, a patient may tap on a medication 1002 to open a message 1004 related to the medication. Such message may include, for example, dosage, instructions for taking the medication (e.g. with/without food), a picture of the bottle and/or pill, etc. In embodiments, the message 1004 may include an indicator button 1006 (e.g. "Done") on which the patient may tap to indicate that the medication has been taken (which may remove the medication from the list). In further embodiments, the message 1004 may include a back button 1008 on which the user may tap to go back to the list 1002. In some embodiments, a pop-up display 1010 of a scheduled medication reminder and/or a skipped/overdue medication may appear on the home screen 700 of the device 300. In some embodiments, the patient may indicate that he/she elects to re-set a time for taking a medication or skip a medication (e.g. via a "skip" 1012 button; see FIG. 10C).

Example of Assistive Service System

Figure 11A:
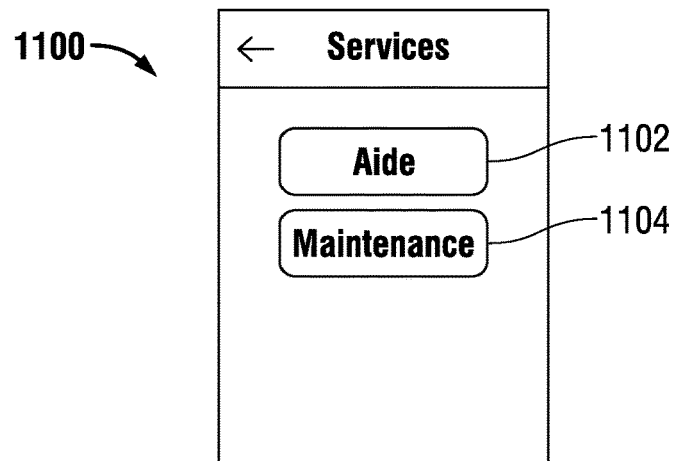
FIGS. 11A-C show various examples of displays for an assistive service system, according to various embodiments.
Figure 11B:
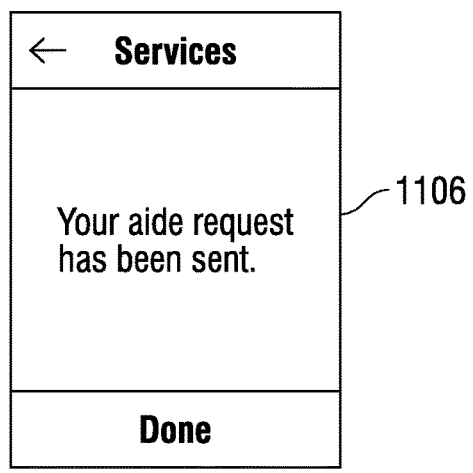
Figure 11C:
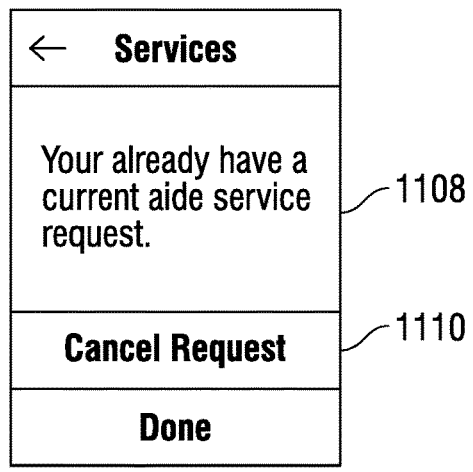

In embodiments, the assistive service system 318 may allow the patient to send direct requests for non-emergency assistance and request maintenance help, as exemplified in FIGS. 11A-C. In embodiments, such requests may be sent to a response agent and/or other caretaker. In some embodiments, the patient may be living in an assisted living/patient care facility and the response agent and/or caretaker may be a worker in the facility.

As exemplified in FIG. 11A, a display 1100 (which may be accessed, for example, by tapping on the "Service" button 722; see FIG. 7D) may show various types of services, e.g.

"Aide" 1102 and "Maintenance" 1104 that a patient may request by tapping on the appropriate button. In embodiments, the request may appear in the active alerts section 500 of the response agent interface system 210 (see FIG. 5B). According to various embodiments, once a request is sent, the patient may receive an acknowledging message 1106 (see FIG. 11B). In some embodiments, if a patient has already sent a request, a message 1108 may be sent notifying the patient that the request is pending (see FIG. 11C). In some embodiments, the patient may have the option to cancel a request 1110. In further embodiments, the response agent/caretaker may send a response (e.g. through interface system 210) to acknowledge the request or communicate other information to the patient.

Example of Personal Contacts Communication System

Figure 12:
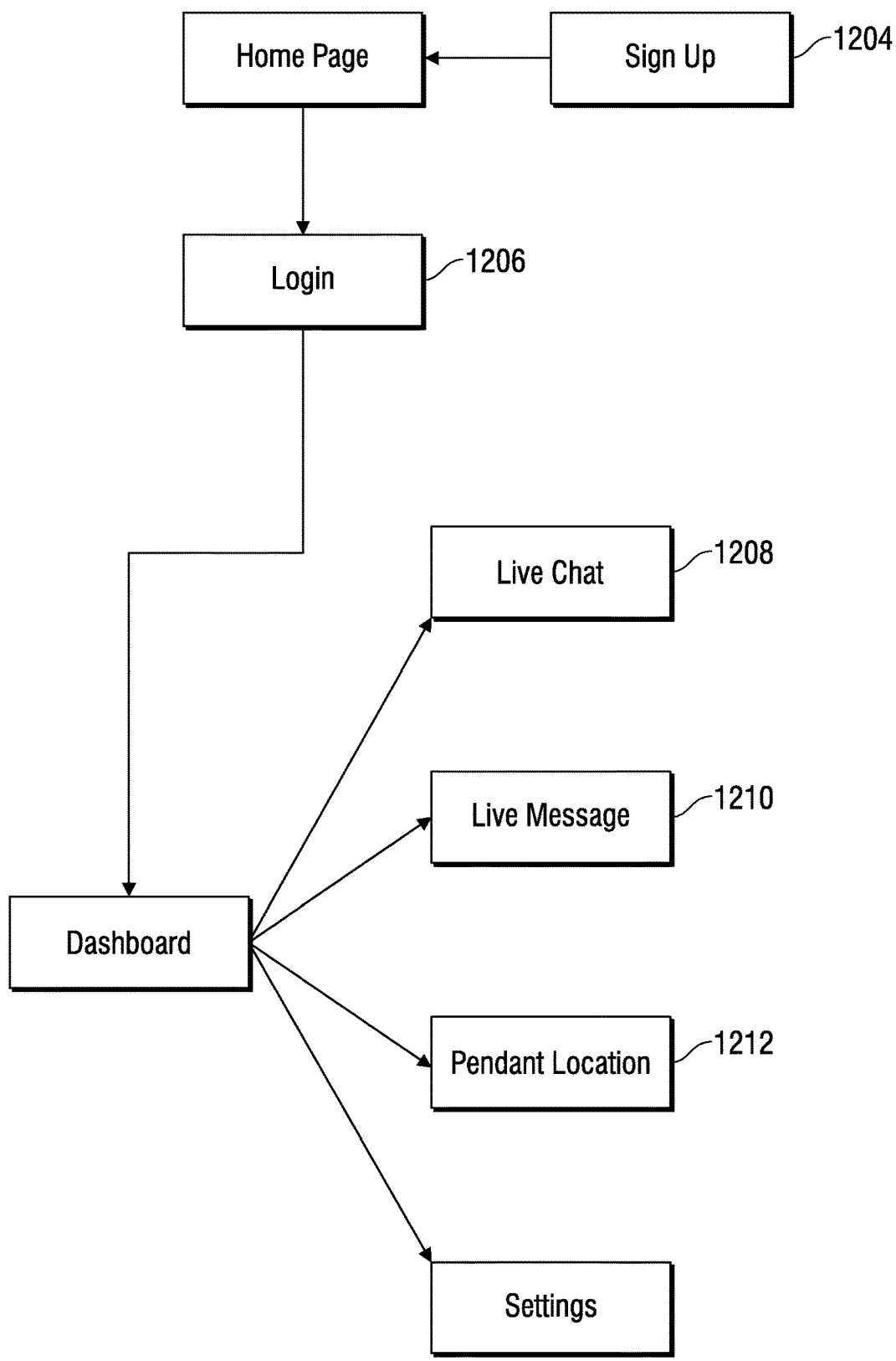
FIG. 12 shows a flow chart for a personal contacts communication system, according to various embodiments.

FIG. 12 shows a flow chart for the personal contacts communication system 320, according to various embodiments. In embodiments, personal contacts communication system 320 may allow individuals who are personal contacts of the patient, such as family members, friends, and other caretakers to communicate with the patient and/or response agent via the device 300. In some embodiments, communication may be through audio and/or video system 1208, and/or through a text messaging system 1210. Additionally, the personal contacts communication system 320 may include a device location system 1212 wherein said individuals may locate the device in order to track the patient, according to various embodiments. In some embodiments, system 320 may include a sign-up system 1204 and/or login system 1206 for registration and verification by the individual(s) wishing to use the personal contacts communication system 320.

Figure 13A:
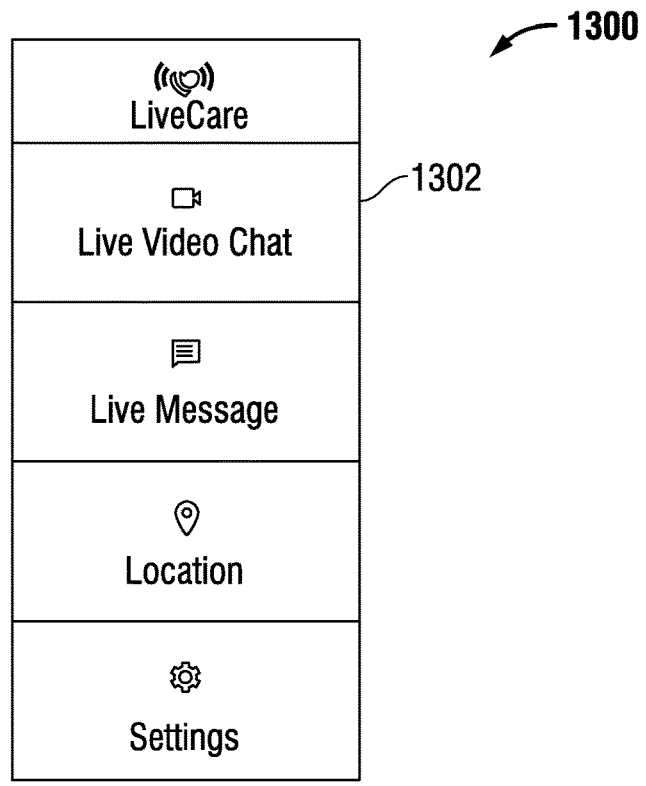
FIG. 13A is an example of a menu display for the personal contacts communication system.
Figure 13B:
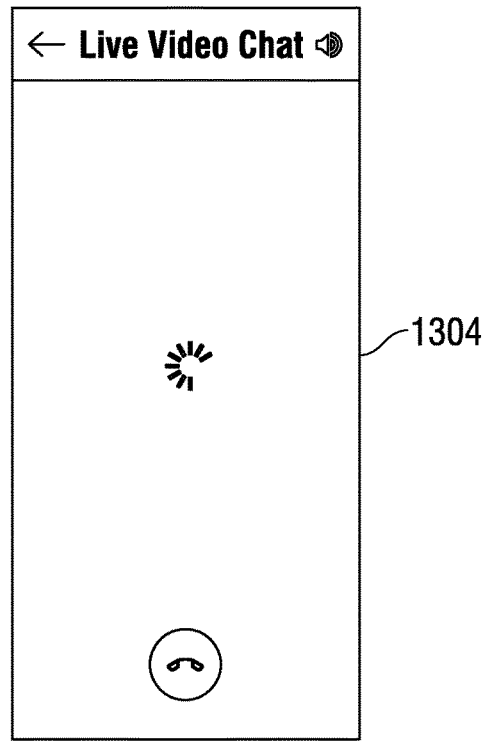
FIG. 13B is an example of a "live video chat" screen for the personal contacts communication system.

As illustrated in FIG. 13A personal contacts communication system 320 may provide a menu display 1300 listing various functions of the personal contacts communication system 320. In embodiments, a user may tap on a function (e.g. "live video chat" 1302, as exemplified in FIG. 13B) to open up a screen 1304 for performing that function.

FIG. 13C shows an exemplary embodiment for an account creation page 1306 which may be used by individuals wishing to communicate with a patient. In embodiments, an individual who has created an account may be required to login (e.g. using an ID/password) and may further be required to identify the patient he/she wishes to engage with.

Service Engagement System

Figure 14:
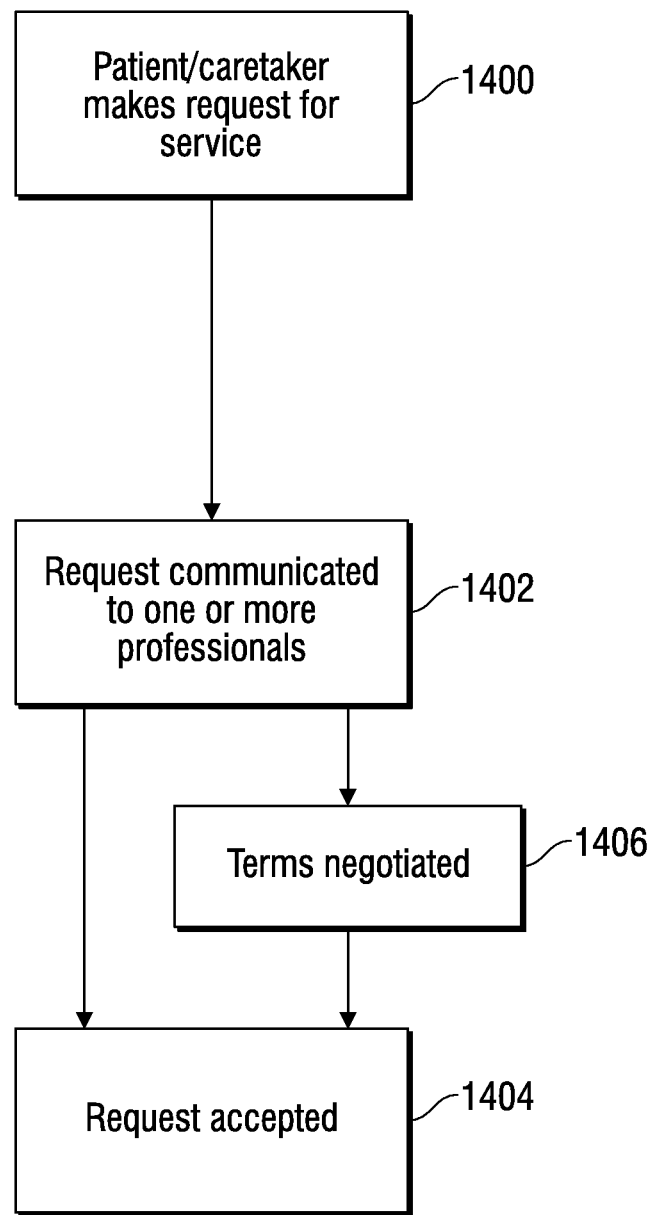
FIG. 14 is a flow chart for a service engagement system, according to various embodiments.

FIG. 14 is a flow chart for a service engagement system 317 which may facilitate a patient in engaging help offered by third party service professional (companies and/or individuals) on an on-call/as-needed basis. The service professionals may offer services from a variety of industries such as housekeeping, food preparation, food delivery, grocery shopping, gardening, salon, physical therapy, chiropractic, massage, transportation, nursing, etc. Such services may be performed at the patient's location or at the professional's business location. In embodiments, the professionals may be pre-enrolled with the service engagement system 317 and/or prescreened. In some embodiments, a fixed fee for a particular service may be prearranged according to the system 317. In other embodiments, the fee may be set and/or agreed upon on an individual basis.

As shown in the figure, a patient and/or caretaker of the patient may make a request 1400 through service engagement system 317 for a service professional in a particular industry. In embodiments, the request may be made through the device 300, though this need not necessarily be the case. In further embodiments, the patient and/or caretaker may specify various terms and conditions relevant to the request (e.g. house call/location, fee, job description, time).

Once a request has been made, service engagement system 317 may communicate the request 1402 to one or more professionals in that industry, who may reply to the request. In some embodiments, the request may be communicated only to professionals who meet certain criteria. Such criteria may include, for example, being located within a certain distance from the patient (i.e. proximity to the patient), being available within a certain time frame, or meeting a patient's specified conditions (e.g. a maximum fee set by the patient).

In further embodiments, the request for service may be automatically accepted 1404 by a professional who is first to respond (e.g. for pre-set fee). In other embodiments, one or more professionals may respond to the request, and may offer terms of service (e.g. price, completion time, etc.) and/or engage in a "bidding" process and/or negotiating terms 1406 for the job, which may then be accepted or countered by the requesting patient and/or caretaker.

Thus, the service engagement system 317, which may be enabled through device 300, may be particularly beneficial to patients living at a private residence (i.e. outside a assisted living facility) to manage daily chores by offering on-call assistance on an as needed basis. Additionally, the service engagement system 317 may, in some cases, substitute or delay the need for a live-in caretaker.

Device

Figure 15:
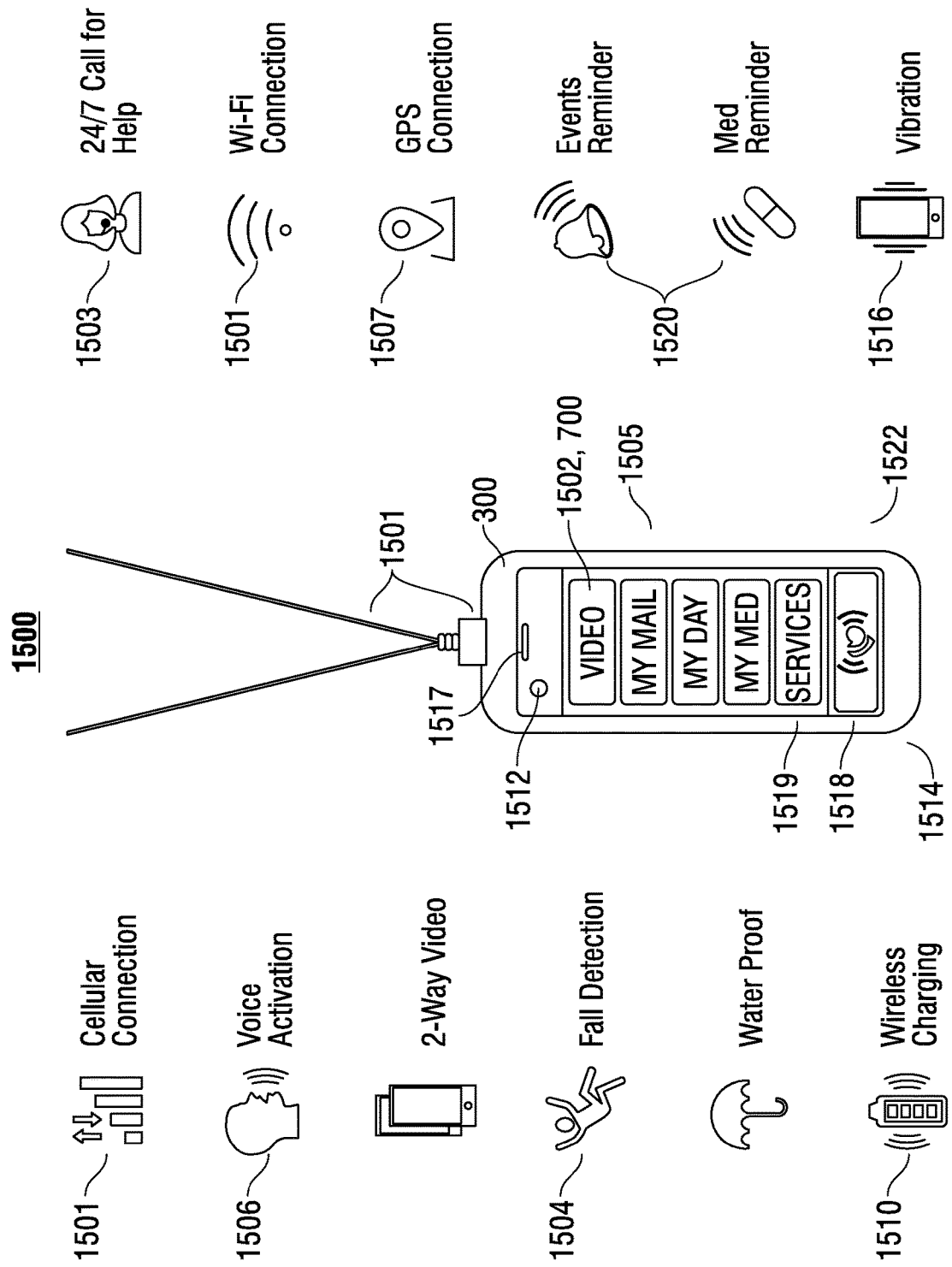
FIG. 15 illustrates a patient care device, which may be used for implementing the patient care method Of FIG. 1, according to various embodiments.

FIGS. 15-23 illustrate a device and device system for implementing patient care method 100, which may be patient care device 300, according to various embodiments. As illustrated in FIG. 15, the device 300 may comprise various functional systems and/or components 1500 including operating electrical and mechanical interfaces that may support the functions and executable instructions related to patient care method 100. Additionally, the device 300 may be portable.

In embodiments, the systems/components 1500 may include one or more data transmission/receiving system(s) 1501, which may be wireless, such as cellular, Wi-Fi, and/or satellite, according to various embodiments.

In embodiments, the systems/components 1500 may include a display screen 1502, which may comprise a touch command interface/touch sensitive display (i.e. capacitive touch screen 700). In further embodiments, the systems/components 1500 may comprise an emergency button 1503. In further embodiments, the systems/components 1500 may comprise a fall detector 1504. In further embodiments, the systems/components 1500 may comprise a motion/orientation sensor 1505. In further embodiments, the systems/components 1500 may comprise a voice command interface system 1506. In further embodiments, the systems/components 1500 may comprise a location tracking/GPS component 1507. In further embodiments, the systems/components 1500 may comprise an attachment system 1508 for enabling the device to be worn by the patient (see FIGS. 17-21). Further functional systems and/or components 1500 may include a device charging system 1510 (see FIG. 20), device camera 1512 (e.g. for enabling two-way video, lighting element 1514, vibration member (i.e. motor) 1516, microphone 1517, speaker 1518, ambient light and distance sensor 1519, and/or alarm system 1520, etc. In some embodiments, the device 300 may be waterproof. In further embodiments, the functional systems and/or components 1500 may comprise a bio signs receiver 1522, which may be configured for receiving and/or transmitting signals from various bio monitors, which may be worn by the patient according to various embodiments. Other functional systems and/or components

1500 may include various physical buttons, such as a menu and/or home button, which may be used for powering the device on/off and/or locking the device, according to various embodiments, In embodiments, other functional systems and/or components may include volume adjustment button(s), a Subscriber Identity Module (SIM) card slot, a head set jack, and a docking/charging external port.

Figure 16:
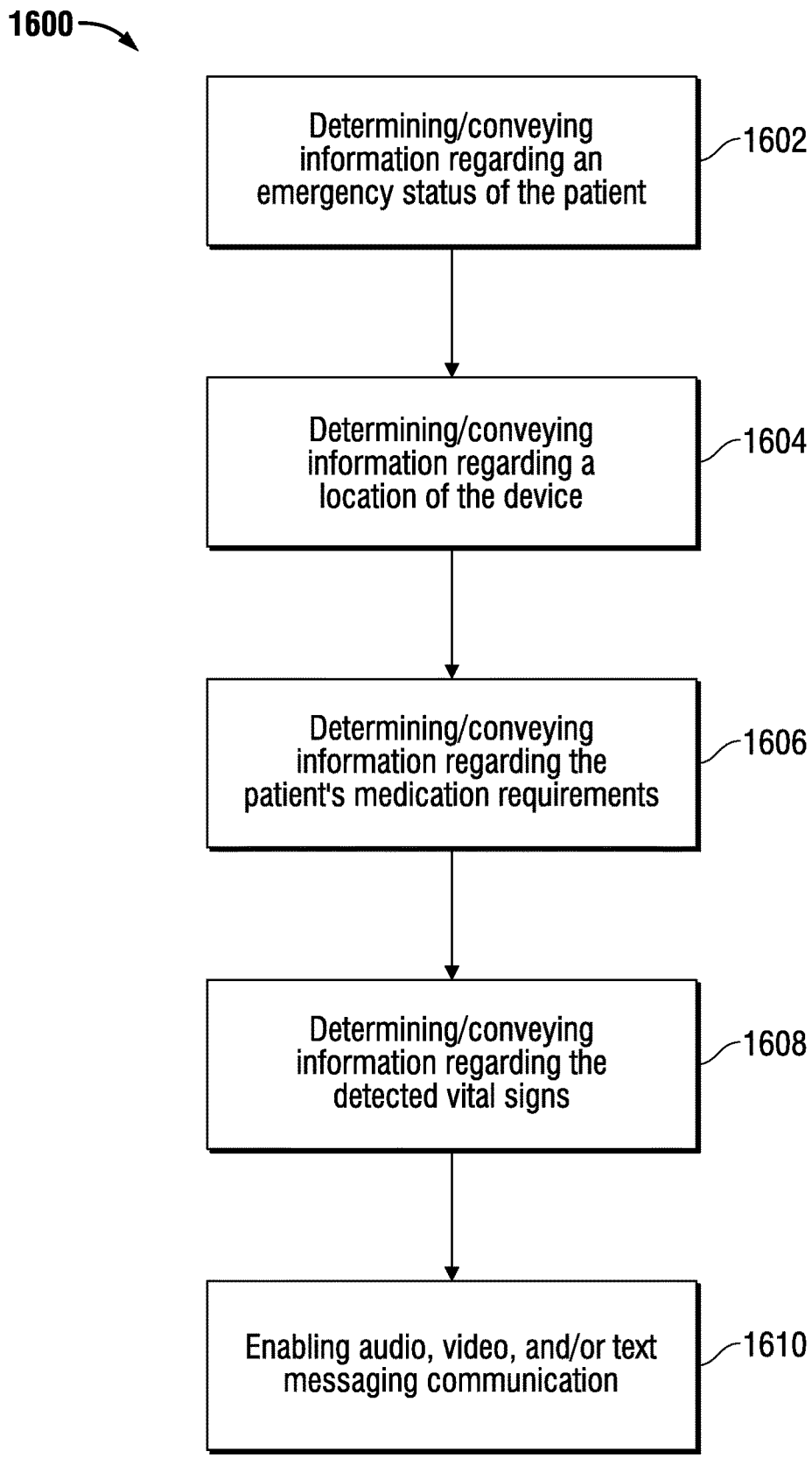
FIG. 16 illustrates various tasks related to the patient care method of FIG. 1, which may be executed by the patient care device of FIG. 15.

Additionally, the device 300 may comprise various processing, control, and memory systems, which may be in communication with one another, and which may be in communication with at least one of the functional systems and/or components 1500 for running primary, smart, and/or background functions 1600 related to patient care method 100, which may be carried out by the response agent/caretaker and/or patient, as shown in FIG. 16.

In embodiments, such functions 1600 related to patient care method 100 may include determining and/or conveying information regarding an emergency status of the patent 1602. In embodiments, determining and conveying information regarding an emergency status of the patient 1602 may comprise receiving a distress indication by the emergency button 1503 (i.e. mechanical trigger system 304), fall detector 1504 (i.e. fall detection system 306), bio signs receiver 1522 (i.e. bio sensor system 305), GPS 1507 (i.e. location tracking system 308, wherein a distress indication may be detection of the patient outside a predetermined location), voice command interface system 1506, and/or touch command interface of touch screen 1502.

In further embodiments, functions 1600 related to patient care method 100 may comprise determining and/or conveying information regarding a location of the device 1604 (i.e. patient wearing the device) for locating and/or determining whether the patient is in safe and/or anticipated location.

In further embodiments, functions 1600 related to patient care method 100 may comprise determining/conveying information regarding the patient's medication requirements 1606. In some embodiments, determining/conveying information regarding the patient's medication requirements 1606 may comprise, sending medication reminders and/or instructions (e.g. by a response agent and/or caretaker) to the patient to be displayed on the touch screen 1502.

Figure 22:
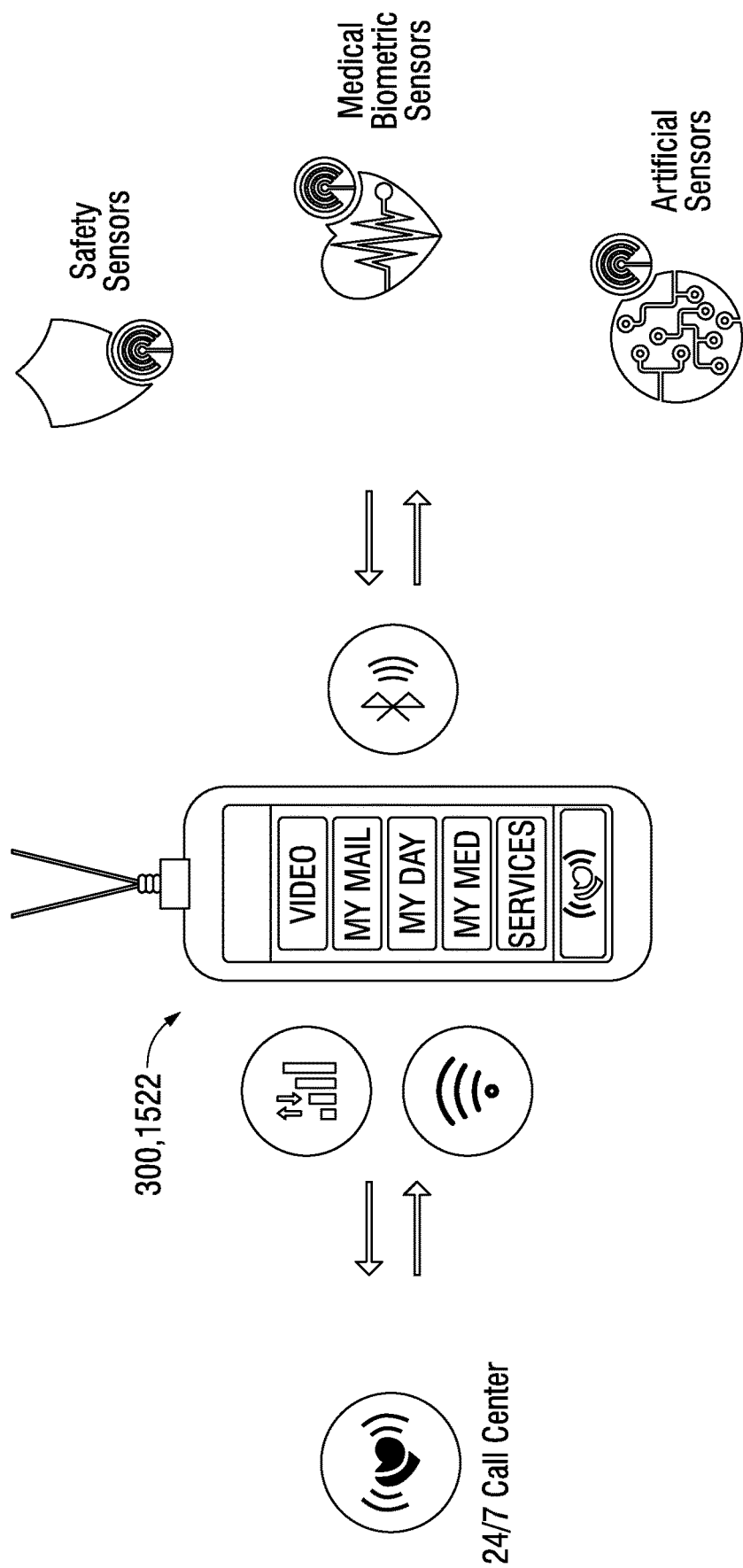
FIG. 22 illustrates a bio monitor system for the device of FIG. 15, according to various embodiments.

In further embodiments, functions 1600 related to patient care method 100 may comprise receiving and/or conveying information regarding the patient's detected bio signs 1608 (see FIG. 22).

In further embodiments, functions 1600 related to patient care method 100 may comprise enabling audio, video and/or text messaging communication 1610 with a response agent or other caretaker, and/or personal contact(s) or other third party.

Figure 17:
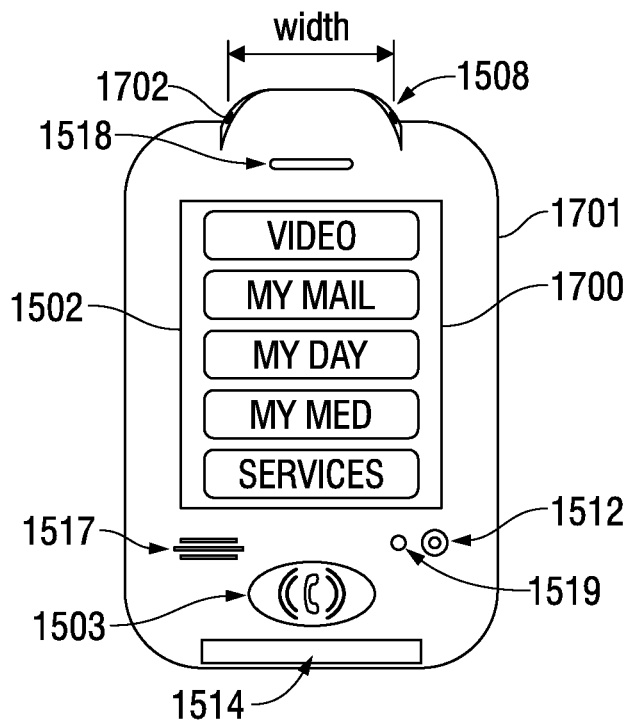
FIG. 17 illustrates the device of FIG. 15, according to a first exemplary embodiment, wherein the device may be worn as a pendant.

In further embodiments, functions 1600 related to patient care method 100 may comprise enabling the patient to access/utilize various utility functions 1612 of the device 300, including non-emergency functional system 310, and the device lighting element 1514 (see FIG. 17).

Thus, the device 300 may be used by a response agent and/or other caretaker, who may be located remotely from the patient, to monitor the status of the patient and respond to the needs of the patient. This may comprise monitoring for an emergency alert status of a patient 103, monitoring a location a patient 104, monitoring activity of a patient 105, monitoring medication needs a patient 106, monitoring bio signs of a patient 107, monitoring non-emergency requests/alerts of a patient 108, accessing patient information 109, responding to an emergency alert 112, responding to a non-emergency request 113, responding to an anticipated need 114 of a patient, communicating 115 with a patient, sending assistance 116 to a patient, and/or contacting and/or connecting the patient with a third party 117, according to various embodiments. Additionally, the device 300 may enable patient interaction 118 with personal contacts, send and receive mail communication, display daily reminders, and/or enable the patient to retain/engage 119 the services of various professionals.

FIG. 17 illustrates a device 300 according to a first exemplary embodiment, wherein the device may be worn as a pendant (i.e. around the neck of a patient). According to various embodiments, and as shown in the figure, the device may have a generally flat rectangular (including square) configuration. The device 300 may comprise emergency button 1503, display screen 1502, and attachment element 1508. According to various embodiments, the device may further comprise lighting element 1514, speaker 1518, microphone 1517, and camera 1512, which are located on a front side 1700 of the device, with the emergency button 1503, display screen 1502, as shown. In some embodiments, the device 300 may comprise an ambient light and distance sensor 1519, or, in other embodiments, the camera 1512 may perform such functions. In some embodiments, a camera may also be provided on a rear side 1701 of the device.

Figure 18A:
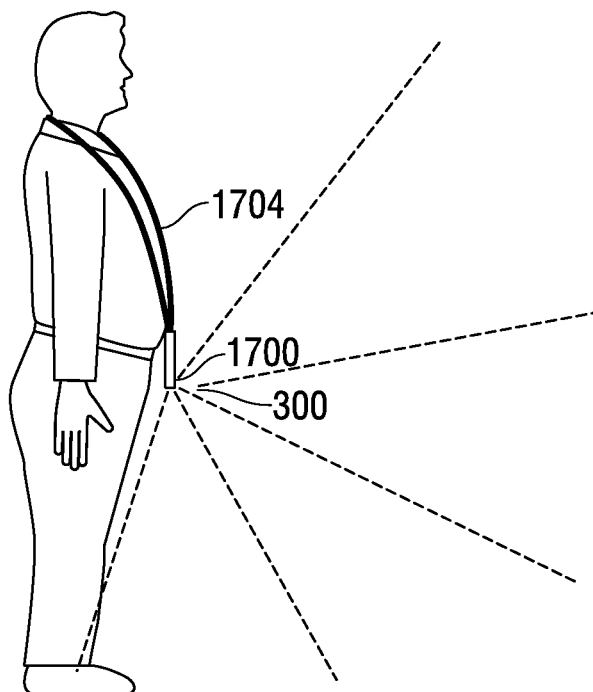
FIG. 18A illustrates the device of FIG. 17 worn by a patient.
Figure 18B:
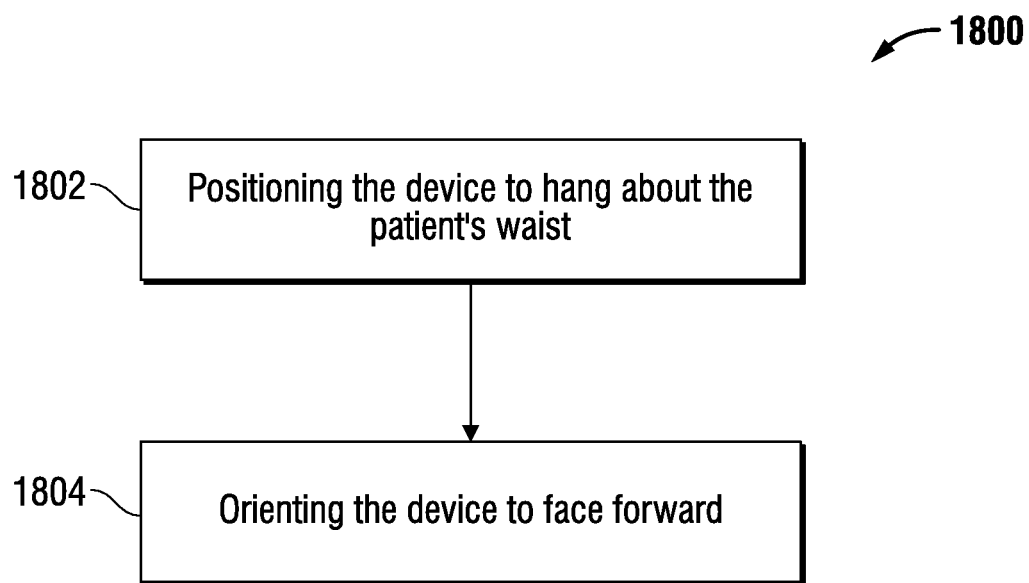
FIG. 18B illustrated a method of using the device of FIG. 17, which may assist the patient in walking.

In embodiments, the attachment element 1508 may include a wide channel 1702, for receiving a necklace/lanyard 1704 for hanging the device 300 around a patient's neck (see FIG. 18A). In some embodiments, the channel 1702 may be on a frame edge, which may be on a short edge of the rectangle, as shown in the figures. In embodiments, the width of the channel 1702 is configured to prevent the device 300 from twisting, and to keep the device facing in one direction, when worn. In embodiments, the channel may have a width, for example, of at least about ¼ of the width of the device. Additionally, the necklace/lanyard 1704 may be size adjustable as described below.

In embodiments, the lighting element 1514 may be configured to provide a walking light, which may assist the patient in walking through dark areas. To this end, the lighting element 1514 may provide high intensity light, and a wide light dispersion angle with uniform lighting and low heat radiation. As such, the lighting element 1514 may be configured to provide illumination for a forward walking path of the patient. In further embodiments, the lighting element 1514 may include intensity control element, which may be local or remote, to adjust the intensity of light in response to varying ambient conditions. In embodiments, the intensity control element may be manual or automatic. In some embodiments, the intensity control element may be automatically controlled by the sensor 1519.

As the device may be worn with the front side 1700 maintained in a forward facing position, the lighting element 1514 may shine light in front of the patient to provide forward illumination, thus assisting the patient while walking in dark areas. Additionally, the emergency button 1503 may be easier for the patient to locate in a front facing position.

As shown in FIGS. 18A and B, a method 1800 of using the device 300 to assist a patient in walking may comprise positioning the device to hang about the patient's waist 1802 (i.e. around a lower section of the abdomen and/or below the abdomen), and orienting the device to face forward 1804 (via attachment element 1508), such that the lighting element is in a forward facing position. This may be achieved by adjusting the size and orientation of the necklace/lanyard 1704 with respect to the device. In this manner, the device is positioned close to the patient's hand and within easy reach. This may be particularly advantageous to patients with limited range of motion and/or limited arm strength. Additionally, positioning the device away from the patient's chest area decreases susceptibility for electrical interference for patients with a pacemaker and/or ECG patch electrodes, and further prevents blocking of the light by the abdomen of obese patients.

Other advantages in positioning the device near the patient's waist including providing a large range over which the patient can adjust the viewing distance to read controls and the touch screen display, and directing light from lighting element 1514 downwards and towards the feet of the patient to enable walking in dimly lit or unlit environments. This may improve visibility and reduce vertigo during walking by reducing the appearance of moving shadows in the patient's visual field.

Figure 19:
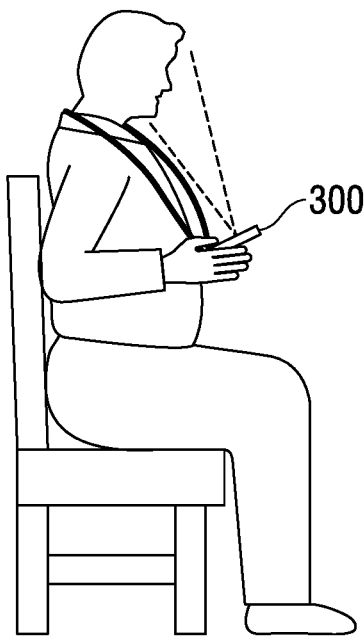
FIG. 19 illustrates the device of FIG. 17 held by a patient.

FIG. 19 illustrates how the device 300 might be oriented when held by the patient. In embodiments, orientation sensor may provide an upright orientation of the screen display. Moreover, in embodiments, the camera 1512 may be located away from the attachment element 1508 to provide an unobstructed view when the device is held by the patient, as shown. Additionally, font positioning of the speaker 1518 and microphone 1517 along with the camera 1512 and lighting element 1514, provides better audio and video quality as these components face the patient while holding the device. Such features, including positioning of the camera, quality and control features of the lighting element 1514 element may further be beneficial in enabling a remote caretaker/response agent the ability to obtain a clear and natural color view of the patient in conducting a remote examination of the patient.

Figure 20:
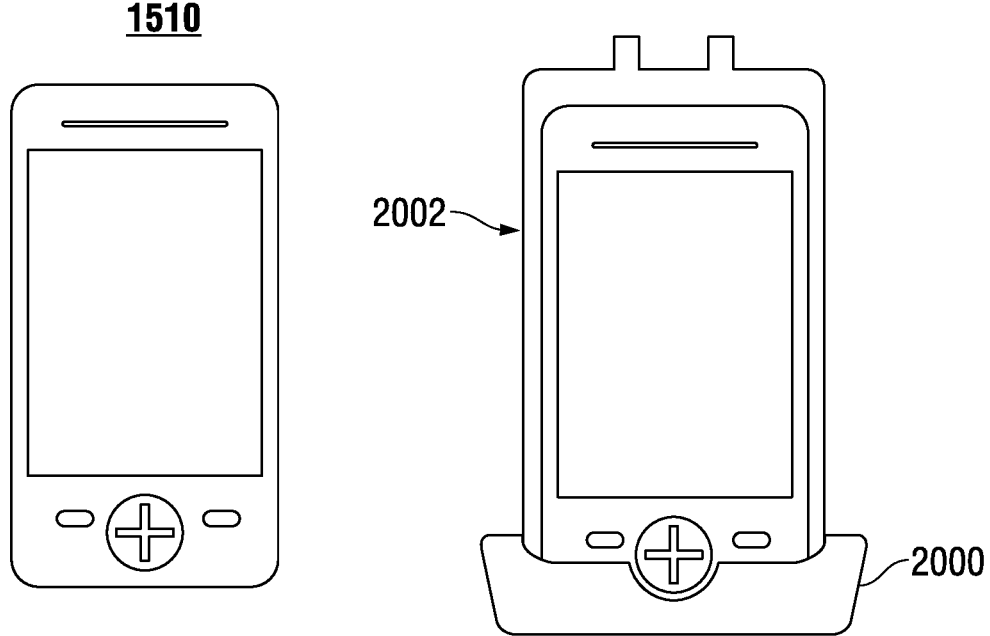
FIG. 20 illustrates a charging system for the device of FIG. 17, according to an exemplary embodiment.

FIG. 20 provides an exemplary embodiment for a charging system for the device 300. In embodiments, charging may be wireless via induction and/or wired via an external charging port. In embodiments, charging system may comprise a base 2000 with slot into which the device may be positioned for charging. In some embodiments, the base 2000 may include a rear panel 2002 which may further include an illumination source, thus serving as a night light. According to various embodiments, the illumination may be automatically controlled (e.g. in response to ambient light) or manually controlled. Additionally, control of the illumination source may be local and/or remote.

Figure 21:
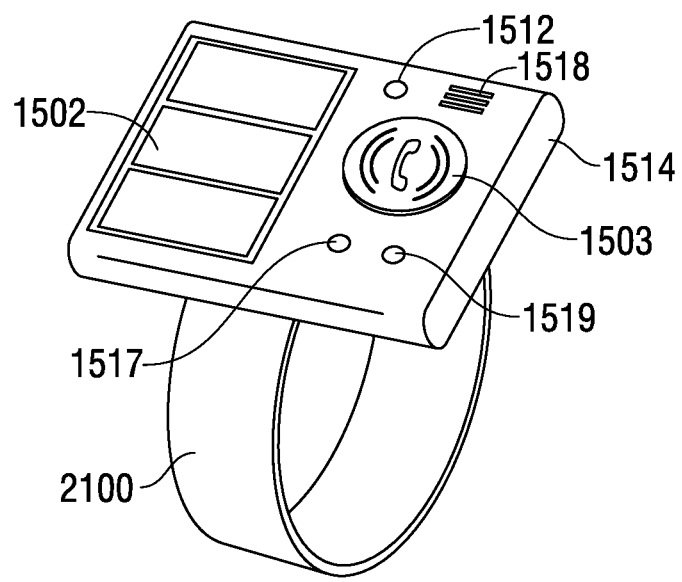
FIG. 21 illustrates the device of FIG. 15, according to a second exemplary embodiment, wherein the device may be worn on a wrist of a patient.

FIG. 21 illustrates the device 300 according to a second exemplary embodiment, wherein the device may be worn as a watch (i.e. on a wrist of a patient). As shown, the device 300 may comprise a wristband 2100, an emergency button 1503, display screen 1502, lighting element 1514, speaker 1518, microphone 1517, and camera 1512, as shown. In some embodiments, the device 300 may comprise an ambient light and distance sensor 1519, or such functions may be provided by the camera 1512.

In the "watch" embodiment, the device may integrate biosensors and sensor electrodes on a back side of the device, such that they are configured to contact the patient's skin. In embodiments, the device may include sensors for measuring heart rate, heart rate variability, blood oxygen saturation (SpO$_2$), temperature, etc.

In some embodiments, the device 300, whether configured to be worn as a pendant, watch, or other accessory/attachment may further include a wear detection system to indicate to the caretaker (i.e. response agent and/or family member), and/or to the patient, that the patient is not wearing the device, should that be the case. This may be achieved, for example, through component(s) such as a motion detector and/or orientation sensor in the device which provides an indication upon detecting lack of motion and/or a unnatural orientation (e.g. a horizontal positioning) for a predetermined and/or prolonged period of time, according to various embodiments. In embodiments, an indication to the patient may comprise, for example, a sound, flashing lights, etc. In embodiments, an indication to the caretaker may be provided, for example, via the response agent interface system 210 or other electronic communication system.

Bio Monitor System

As illustrated in FIG. 22, biosensor system may comprise a variety of sensors (bio-monitors) for monitoring bio signs of the patient, which may be embedded/integrated with device 300 and/or in communication with the device, i.e. bio sign receiver 1522 of the device. According to various embodiments, such sensors may be paired with the device 300 for transmitting data to the device. In embodiments, such sensors may establish short-range communication and/or be paired with the device via a Bluetooth connection. Examples include sensors for monitoring various vital signs such as heart rate, blood pressure, oxygen level, glucose, etc., and various other biosensors, which are or may become available with emerging technology. Thus, the device 300 may act as a "hub" for monitoring bio signs received from multiple sensors which may be paired with the device.

In some embodiments, biosensor(s) may be worn by the patient, and transmit continuous or intermittent readings to the device. In some embodiments, the device may be configured to transmit all information received from the biosensor to the response agent system 208 and/or to the patient database of the system. In some embodiments, the device may be configured to transmit information on an intermittent basis, and/or upon detection of an unusual reading. In embodiments, an unusual reading may be a reading outside a standard normal range and/or a reading which significantly diverges (e.g. based on statistical criteria) from previous readings for the patient. In some embodiments, the device may be configured to convey an emergency alert upon sensing an unusual reading. In some embodiments, the device may provide health alerts and/or health maintenance information to the patient based on the bio-readings.

Figure 23:
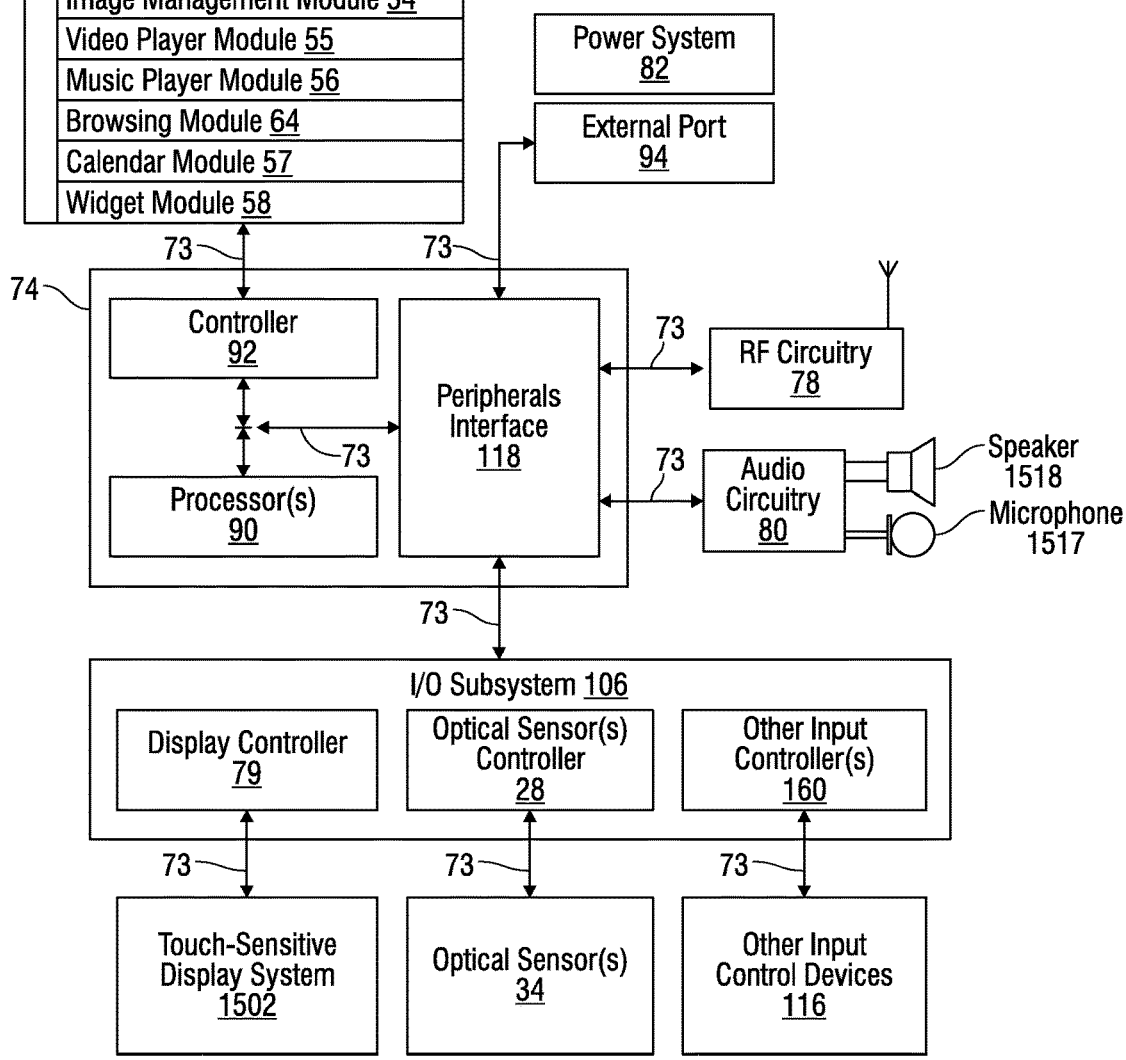
FIG. 23 is a block diagram of internal component circuits of the device of FIG. 15.

FIG. 23 depicts a block diagram of internal component circuits of the patient care device 300 that may support the data and executable instructions of the presently disclosed subject matter, including running primary, smart, and/or background functions 1600 related to patient care method 100 according to various embodiments.

In embodiments, patient care device 300 may include memory 72 (which may include one or more computer readable storage mediums); memory controller 92; one or more processing units (CPU's)/processor 90; peripherals interface 88; RF circuitry 78; audio circuitry 80, (which may be coupled to microphone 1517, speaker 1518); input/output (I/O) subsystem 76, including display controller 79 which may be in communication with touch sensitive display system/touch screen 1502, optical sensor(s) controller 28 which may be in communication with optical sensor(s) 34, other input control devices 86 which may be in communication with other input control devices 86; and external port 94. These components may communicate over one or more communication buses or signal lines 73 and may provide various functional systems and/or components 1500 of patient care device 300.

It should be appreciated that patient care device 300 is only one example of an applicable device and that patient care device 300 may have more or fewer components than shown, may combine two or more components, or a may have a different configuration or arrangement of the components. The various components/systems shown in FIG. 23 may be implemented in hardware, software or a combination of both hardware and software, including one or more signal processing and/or application specific integrated circuits.

In embodiments, memory 72 may include high-speed random-access memory and may also include non-volatile memory, such as one or more magnetic disk storage devices, flash memory devices, or other non-volatile solid-state memory devices. Access to memory 72 by other components of patient care device 300, such as the processors 90 and peripherals interface 88, may be controlled by the memory controller 92, according to various embodiments.

In embodiments, peripherals interface 88 may couple the input and output peripherals of the device to the processors 90 and memory 72. The one or more processor(s) 90 may run or execute various software programs and/or sets of instructions stored in memory 72 to perform various functions for patient care device 300 and to process data.

In some embodiments, peripherals interface 88, processor(s) 90, and memory controller 92 may be implemented on a single chip, such as a chip 74. In some other embodiments, they may be implemented on separate chips.

In embodiments, RF (radio frequency) circuitry 78 may receive and send RF signals, also called electromagnetic signals. RF circuitry 78 may convert electrical signals to/from electromagnetic signals and communicate with communications networks and other communications devices via the electromagnetic signals. RF circuitry 78 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth.

In embodiments, RF circuitry 78 may comprise and/or be configured to communicate with bio signs receiver 1522 for receiving and/or transmitting signals from various bio monitors for running vital sensor system 305. In embodiments, RF circuitry 78 may comprise and/or be configured to communicate with GPS component 1507. In embodiments, RF circuitry 78 may comprise and/or be configured to communicate with one or more data transmission/receiving system(s) 1501. In embodiments, RF circuitry 78 may be configured to communicate with various devices and/or networks. For example, RF circuitry 78 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.16, IEEE 802.11g and/or IEEE 802.11n), voice over Internet Protocol (voip), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

Audio circuitry 80, speaker 1518, and microphone 1517 provide an audio interface between a user and device 300, and may provide various functional systems and/or components 1500 of patient care device 300 such as voice command interface system 1506, alarm system 1520, according to various embodiments. In embodiments, Audio circuitry 80 receives audio data from peripherals interface 88, converts the audio data to an electrical signal, and transmits the electrical signal to speaker 1518. Speaker 1518 converts the electrical signal to human-audible sound waves. Audio circuitry 80 also receives electrical signals converted by microphone 1517 from sound waves. Audio circuitry 80 converts the electrical signal to audio data and transmits the audio data to peripherals interface 88 for processing. Audio data may be retrieved from and/or transmitted to memory 72 and/or RF circuitry 78 by peripherals interface 88. In some embodiments, audio circuitry 80 may also include a headset jack. The headset jack may provide an interface between audio circuitry 80 and removable audio input/output peripherals, such as output-only headphones or a headset with both output (e.g., a headphone for one or both ears) and input (e.g., a microphone).

I/O subsystem 76 couples input/output peripherals on patient care device 300, such as display screen 1502 and other input/control devices 86, to peripherals interface 88. In embodiments, I/O subsystem 76 may include a display controller 79 and one or more input controllers 77 for other input or control devices 86.

In embodiments, one or more input controllers 77 receive/send electrical signals from/to other input or control devices 86. According to various embodiments, such other input/control devices 86 may include emergency button 1503, fall detector 1504, motion/orientation sensor 1505, lighting element 1514, vibration member (i.e. motor) 1514, and various other devices such as accelerometer(s), proximity sensor(s), etc.

Thus, RF circuitry 78 in conjunction with data transmission/receiving system(s) 1501, bio signs receiver 1522, GPS component 1507, emergency button 1503, fall detector 1504, and/or motion/orientation sensor 1505 may provide emergency activation system 302 of the device 300.

In some embodiments, other input/control devices 86 may include other physical buttons, e.g. such as an up/down button for volume control of speaker 1518 and/or microphone 1517, an unlock and/or on/off button may be included. In some embodiments, the user may be able to customize a functionality of one or more of the buttons. In embodiments, touch screen 1502 may be used to implement virtual or soft buttons and one or more soft keyboards. In some alternate embodiments, input controller(s) 77 may be coupled to any (or none) of the following: a keyboard, infrared port, USB port, and a pointer device such as a mouse.

Touch-sensitive touch screen 1502 may provide an input interface and an output interface between patient care device 300 and a user. Display controller 79 may receive and/or send electrical signals from/to touch screen 1502. Touch screen 1502 may display visual output to the user. The visual output may include graphics, text, icons, video, and any combination thereof (collectively termed "graphics"). In some embodiments, some or all of the visual output may correspond to user-interface objects.

Touch screen 1502 has a touch-sensitive surface, sensor or set of sensors that accepts input from the user based on haptic and/or tactile contact. Touch screen 1502 and display controller 79 (along with any associated modules and/or sets of instructions in memory 72) detect contact (and any movement or breaking of the contact) on touch screen 1502 and converts the detected contact into interaction with user-interface objects (e.g., one or more soft keys, icons, web pages or images) that are displayed on the touch screen. In an exemplary embodiment, a point of contact between a touch screen 1502 and the user corresponds to a finger of the user.

Touch screen 1502 may use LCD (liquid crystal display) technology, or LPD (light emitting polymer display) technology, although other display technologies may be used in other embodiments. Touch screen 1502 and display controller 79 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 1502.

The touch screen 1502 may have a resolution in excess of 100 dpi. In an exemplary embodiment, the touch screen has a resolution of approximately 160 dpi. The user may make contact with touch screen 1502 using any suitable object or appendage, such as a stylus, a finger, and so forth. In some embodiments, the user interface is designed to work primarily with finger-based contacts and gestures, which are much less precise than stylus-based input due to the larger area of contact of a finger on the touch screen. In some embodiments, the device translates the rough finger-based input into a precise pointer/cursor position or command for performing the actions desired by the user weak.

In some embodiments, in addition to the touch screen, patient care device 300 may include a touchpad (not shown) for activating or deactivating particular functions. In some embodiments, the touchpad is a touch-sensitive area of the device that, unlike the touch screen, does not display visual output. The touchpad may be a touch-sensitive surface that is separate from touch screen 1502 or an extension of the touch-sensitive surface formed by the touch screen.

In embodiments, patient care device 300 may also include a power system 82, and may further include external port 94, which may provide charging system 1510.

Power system 82 may include a power management system, one or more power sources (e.g., battery, alternating current (AC)), a recharging system, an inductive charging system, a power failure detection circuit, a power converter or inverter, a power status indicator (e.g., a light-emitting diode (LED)) and any other components associated with the generation, management and distribution of power in portable devices.

In embodiments, patient care device 300 may also include one or more optical sensors 34 coupled to optical sensor controller 28 in I/O subsystem 76, which may provide various functional systems and/or components 1500 of patient care device 300 such as the device camera 1512, and/or ambient light and distance sensor 1519.

In embodiments, optical sensor 34 may include charge-coupled device (CCD) or complementary metal-oxide semiconductor (CMOS) phototransistors. Optical sensor 34 may receive light from the environment, projected through one or more lens, and converts the light to data representing an image. In conjunction with an imaging module 53 (also called a camera module), optical sensor 34 may capture still images or video. In some embodiments, optical sensor 34 may be located on the front of the device 300 so that the user's image may be obtained for videoconferencing while the user views the other video conference participants on the touch screen display. In some embodiments, optical sensor 34 may be located on both the front and back sides of the device 300. In some embodiments, the position of optical sensor 34 can be changed by the user (e.g., by rotating the lens and the sensor in the device housing).

In some embodiments, the software components stored in memory 72 may include an operating system 96, a communication module (or set of instructions) 98, a contact/motion module (or set of instructions) 99, a graphics module (or set of instructions) 93, a text input module (or set of instructions) 60, a Global Positioning System (GPS) module (or set of instructions) 61, and applications (or set of instructions) 62.

Operating system 96 (e.g., Darwin, RTXC, LINUX, UNIX, OS X, WINDOWS, or an embedded operating system such as vxworks) includes various software components and/or drivers for controlling and managing general system tasks (e.g., memory management, storage device control, power management, etc.) And facilitates communication between various hardware and software components.

Communication module 98 facilitates communication with other devices over one or more external ports 94 and also includes various software components for handling data received by RF circuitry 78 and/or external port 94. External port 94 (e.g., Universal Serial Bus (USB), FIREWIRE, etc.) Is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with the 30-pin connector used on iPod (trademark of Apple Computer, Inc.) Devices.

Contact/motion module 99 may detect contact with touch screen 1502 (in conjunction with display controller 79) and, in some embodiments, other touch sensitive devices (e.g., emergency button 1503, a touchpad or other physical control elements, physical click wheel, etc.). Contact/motion module 99 may include various software components for performing various operations related to detection of contact, such as determining if contact has occurred, determining if there is movement of the contact and tracking the movement across touch screen 1502, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multitouch"/"multiple finger" contacts).

In some embodiments, the contact/motion module 99 and display controller 79 also detects contact on a touchpad. In some embodiments, contact/motion module 99 and controller 79 may detect contact on emergency button 1503, and other buttons which may be incorporated with device 300.

In embodiments, graphics module 93 includes various known software components for rendering and displaying graphics on touch screen 1502, including components for changing the intensity of graphics that are displayed. As used herein, the term "graphics" includes any object that can be displayed to a user, including without limitation text, web pages, icons (such as user-interface objects including soft keys), digital images, videos, animations and the like. An animation in this context is a display of a sequence of images that gives the appearance of movement and informs the user of an action that has been performed (such as moving an email message to a folder). In this context, a respective animation that confirms an action by the user of the device typically takes a predefined, finite amount of time, such as an amount of time between 0.2 and 1.0 seconds, or between 0.5 and 2.0 seconds, depending on the context.

In embodiments, text input module 60, which may be a component of graphics module 93, provides soft keyboards for entering text in various applications (e.g., contacts 67, e-mail 68, IM 69, notes 63, browser 64, and any other application that needs text input).

In embodiments, GPS module 61 determines the location of the device and may provide this information for use in various functions/systems related to patient care method 100, such as monitoring a location of a patient 104, location tracking system 308, and/or professional service engagement system 317.

In some embodiments, GPS module 61 may provide location information for various other applications (e.g. location-based dialing, to camera module 53 and/or blogging module 63 as picture/video metadata, to applications that provide location-based services such as weather widgets, local yellow page widgets, and map/navigation widgets, etc.).

According to various embodiments, the applications 62 may include the following modules (or sets of instructions), or a subset or superset thereof:

A contacts module 67 (sometimes called an address book or contact list);
A telephone module 65;
A video conferencing module 66;
An e-mail client module 68;
An instant messaging (IM) module 69;
A notes module 63;
A camera module 53 for still and/or video images;
An image management module 54;
A video player module 55;
A music player module 56;
A browser module 64;
A calendar module 57;
Widget modules 58, which may include weather widget 58-1, stocks widget 58-2, calculator widget 58-3, alarm clock widget 58-4, dictionary widget 58-5, and other widgets obtained by the user, as well as user-created widgets 58-6;
A Widget creator module 59 for making user-created widgets 58-6; and
A Search module 51.

Examples of other applications 62 that may be stored in memory 72 include other word processing applications, JAVA-enabled applications, encryption, digital rights management, voice recognition, voice replication, a blogging application, a maps application, etc.

According to various embodiments, applications 62 may be used for implementing various functions 1600 related to patient care method 100, examples of which are described below.

In conjunction with touch screen 1502, display controller 79, contact module 99, graphics module 93, and text input module 64, contacts module 67 may be used to manage/implement various functions 1600 related to patient care method 100, such as the non-emergency function system 310 and/or non-emergency patient utility system 313 (i.e. daily schedule system 312, mail system 314, medications reminder system 316, assistive service system 318, and/or personal contacts communication system 320.

For example, contacts module 67 may be used to manage an address book or contact list, including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications via the telephone module 65, video conference module 66, e-mail 68, or IM 69; and so forth for running mail system 314 and/or personal contacts communication system 320, according to various embodiments.

In conjunction with RF circuitry 78, audio circuitry 80, speaker 1518, microphone 83, touch screen 1502, display controller 79, contacts module 67, graphics module 92, and text input module 60, telephone module 65 may be used to enter a sequence of characters corresponding to a telephone number, access one or more telephone numbers in contacts 67, modify a telephone number that has been entered, dial a respective telephone number, conduct a conversation and disconnect or hang up when the conversation is completed, according to various embodiments. As noted above, the wireless communication may use any of a plurality of communications standards, protocols and technologies.

In conjunction with RF circuitry 78, audio circuitry 80, speaker 1518, microphone 1517, touch screen 1502, display controller 79, optical sensor 34, optical sensor controller 28, contact module 99, graphics module 93, text input module 60, and telephone module 65, videoconferencing module 66 may be used to initiate, conduct, and terminate a video conference between a user and one or more other participants.

In conjunction with RF circuitry 78, touch screen 1502, display controller 79, contacts module 67, graphics module 92, and text input module 60, e-mail client module 68 may be used to create, send, receive, and manage e-mail. In conjunction with image management module 54, e-mail module 68 allows users to create and send e-mails with still or video images taken with camera module 53.

In conjunction with RF circuitry 78, touch screen 1502, display controller 79, contacts module 67, graphics module 92, and text input module 60, instant messaging module 69 may be used to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages and to view received instant messages. In some embodiments, transmitted and/or received instant messages may include graphics, photos, audio files, video files and/or other attachments as are supported in a MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with touch screen 1502, display controller 79, contact module 99, graphics module 92, text input module 60, and camera module 53, image management module 54 may be used to arrange, modify or otherwise manipulate, label, delete, present (e.g., in a digital slide show or album), and store still and/or video images.

In conjunction with touch screen 1502, display controller 79, contact module 99, graphics module 93, audio circuitry 80, and speaker 1518, video player module 55 may be used to display, present or otherwise play back videos (e.g., on the touch screen or on an external, connected display via external port 94).

In conjunction with RF circuitry 78, touch screen 1502, display system controller 79, contacts module 67, graphics module 93, text input module 60, e-mail module 68, and browser module 64, calendar module 57 may be used to create, display, modify, and store calendars and data associated with calendars (e.g., calendar entries, to do lists, etc.).

In conjunction with RF circuitry 78, touch screen 1502, display system controller 79, contacts module 99, graphics module 93, text input module 60, and browser module 64, the widget modules 58 are mini-applications that may be downloaded and used by a user (e.g., weather widget 58-1, stocks widget 58-2, calculator widget 58-3, alarm clock widget 58-4, and dictionary widget 58-5, etc.) or created by the user (e.g., user-created widget 58-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 78, touch screen 1502, display system controller 79, contacts module 99, graphics module 92, text input module 60, and browser module 64, widget creator module 59 may be used by a user to create widgets (e.g., turning a user-specified portion of a web page into a widget).

In conjunction with touch screen 1502, display controller 79, contact module 99, graphics module 93, and text input module 60, notes module 63 a daily system may be used to create and manage notes, to do lists, and the like, for running daily schedule system 312 and/or medications reminder system 316 for example.

Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments. For example, video player module 55 may be combined with music player module 56 into a single module (e.g., a video and music player module). In some embodiments, memory 72 may store a subset of the modules and data structures identified above. Furthermore, memory 72 may store additional modules and data structures not described above.

In some embodiments, operation of a predefined set of functions on the device 300 may be performed through touch screen 1502. Such functions that may be performed through the touch screen may include navigation between user interfaces, and navigation to a main, home, or root menu from any user interface that may be displayed on the device 300. In such embodiments, the touchpad may be referred to as a "menu button." In some other embodiments, the menu button may be a physical push button or other physical input/control device instead of a touchpad.

The methods, systems, process flows and logic of disclosed subject matter associated with a computer readable medium may be described in the general context of computer-executable instructions, such as, for example, program modules, which may be executed by a computer device. Generally, program modules may include routines, programs, objects, components, data structures, etc. that perform particular tasks or implement particular abstract data types. Such modules are typically stored on a data storage media of the host computer device that is remotely or locally situated. The disclosed subject matter may also be practiced in distributed computing environments wherein tasks are performed by remote processing devices that are linked through a communications network. In a distributed computing environment, program modules may be located in local and/or remote computer storage media including memory storage devices.

The detailed description set forth herein in connection with the appended drawings may be intended as a description of exemplary embodiments in which the presently disclosed subject matter may be practiced. The term "exemplary" used throughout this description means "serving as an example, instance, or illustration," and should not necessarily be construed as preferred or advantageous over other embodiments.

This detailed description of illustrative embodiments includes specific details for providing a thorough understanding of the presently disclosed subject matter. However, it will be apparent to those skilled in the art that the presently disclosed subject matter may be practiced without these specific details. In some instances, well-known structures and devices are shown in block diagram form in order to avoid obscuring the concepts of the presently disclosed method and system.

The foregoing description of embodiments may be provided to enable any person skilled in the art to make and use the subject matter. Various modifications to these embodiments will be readily apparent to those skilled in the art, and the novel principles and subject matter disclosed herein may be applied to other embodiments without the use of the innovative faculty. The claimed subject matter set forth in the claims may be not intended to be limited to the embodiments shown herein, but may be to be accorded the widest scope consistent with the principles and novel features disclosed herein. It may be contemplated that additional embodiments are within the spirit and true scope of the disclosed subject matter.

Systems and methods are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the invention. The scope of the invention is accordingly to be limited by nothing other than the appended claims, in which reference to an element in the singular is not intended to mean "one and only one" unless explicitly so stated, but rather "one or more". Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for". As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

It will be appreciated that variations of the above-disclosed and other features and functions, or alternatives thereof, may be desirably combined into many other different systems or applications. Also that various, presently unforeseen or unanticipated, alternatives, modifications, variations or improvements therein may be subsequently made by those skilled in the art which are also intended to be encompassed by the following claims.

The detailed description set forth herein in connection with the appended drawings may be intended as a description of exemplary embodiments in which the presently disclosed subject matter may be practiced. The term "exemplary" used throughout this description means "serving as an example, instance, or illustration," and should not necessarily be construed as preferred or advantageous over other embodiments.

This detailed description of illustrative embodiments includes specific details for providing a thorough understanding of the presently disclosed subject matter. However, it will be apparent to those skilled in the art that the presently disclosed subject matter may be practiced without these specific details. In some instances, well-known structures and devices are shown in block diagram form in order to avoid obscuring the concepts of the presently disclosed apparatus.

The foregoing description of embodiments may be provided to enable any person skilled in the art to make and use the subject matter. Various modifications to these embodiments will be readily apparent to those skilled in the art, and the novel principles and subject matter disclosed herein may be applied to other embodiments without the use of the innovative faculty. The claimed subject matter set forth in the claims may be not intended to be limited to the embodiments shown herein, but may be to be accorded the widest scope consistent with the principles and novel features disclosed herein. It may be contemplated that additional embodiments are within the spirit and true scope of the disclosed subject matter.

What may be claimed is:

1. A patient care device comprising:
   an attachment element, configured to physically attach the device to a patient, such that the device can be worn around the patient's neck as a pendant;
   a communication system configured to enable voice and visual communication through said device;
   a display screen;
   an emergency activation system configured to indicate a potential emergency situation of the patient, said emergency activation system comprising at least one of a mechanical trigger system, a virtual trigger system, a fall detection system, a location tracking system, a bio monitoring system or a combination thereof; and
   a wear detection system, wherein, when the device is not worn by the patient, said wear detection system is configured to provide an indication that the patient is not wearing the device.

2. The patient care device of claim 1, wherein said voice and visual communication can be automatically enabled without patient activation through the device.

3. The patient care device of claim 1, wherein the device has a generally flat configuration including a front side and a back side, wherein the attachment element comprises a channel for receiving a lanyard, such that the lanyard can be looped around the patient's neck with the device suspended from the lanyard, wherein a width of the channel is configured to prevent the device from twisting, and to keep the device facing in one direction when suspended by the lanyard and worn around the patient's neck.

4. The patient care device of claim 3, further comprising a lighting element located on the font side, wherein the lighting element is configured to shine light in front of the patient when the patient is wearing the device with the front side facing forward, such that the lighting element provides illumination for a forward walking path of the patient.

5. The patient care device of claim 4, further comprising a lighting control element configured to control an intensity of the lighting element, wherein the lighting control element is operated manually and/or is configured to automatically adjust the illumination intensity in response to ambient conditions.

6. The patient care device of claim 5, wherein the lighting element can be remotely controlled by the lighting control element.

7. The patient care device of claim 3, wherein the device comprises a speaker and microphone located on the front side of the device; and a location tracking element.

8. The patient care device of claim 3, wherein the emergency activation system comprises a button, wherein the button is located on the front side of the device.

9. The patient care device of claim 3, wherein the device further comprises a lighting element, a speaker, microphone, and at least one camera, which are positioned on the front side of the device.

10. The patient care device of claim 3, further comprising a lanyard engaged through said channel, wherein said lanyard is configured to loop and the patient's neck for suspending the device, wherein said lanyard is size adjustable and/or sized to position the device to hang around a lower section of the patient's abdomen and/or below the patient's abdomen.

11. The patient care device of claim 1, wherein the emergency activation element comprises a mechanical trigger system, said mechanical trigger system comprising a button.

12. A patient care system, comprising:
   a patient care device configured to be worn by the patient, comprising:
      an attachment element, configured to physically attach the device to the patient,
      a communication system configured to enable voice and visual communication through said device,
      a display screen, and
      an emergency activation system configured to indicate a potential emergency situation of the patient, said emergency activation system comprising a mechanical trigger system, and at least one of a virtual trigger system, a fall detection system, a location tracking system, a bio monitoring system, a response system, configured to monitor for and respond to an indication of a potential emergency situation; and a wear detection system, wherein, when the device is not worn by the patient, said wear detection system is configured to provide an indication that the patient is not wearing the device.

13. The patient care system of claim 12, further comprising a lighting element.

14. The patient care system of claim 12, wherein the device can be worn as a watch and/or as a pendant.

15. The patient care system of claim 12, wherein said voice and visual communication can be automatically enabled without patient activation through the device.

16. A patient care method, comprising:

wearing a patient care device, the device comprising:

an attachment element, configured enable the device to be worn, a communication system configured to enable voice and visual communication through said device, a display screen, an emergency activation system configured to indicate a potential emergency situation of the patient, said emergency activation system comprising a mechanical trigger system, and at least one of a virtual trigger system, a fall detection system, a location tracking system, a bio monitoring system, and a wear detection system, wherein, when the device is not worn by the patient, said wear detection system is configured to provide an indication that the patient is not wearing the device.

17. The patient care method of claim 16, wherein wearing the device comprises hanging the device via a lanyard looped around the neck and attached to the device, and positioning the device to hang around a lower section of the abdomen and/or below the abdomen.

18. The patient care method of claim 17, wherein the device further comprises a lighting element, wherein the lighting element is positioned at a front side of the device, wherein wearing the device further comprises orienting the device such that the lighting element is forward facing, the method further comprising using the device to provide illumination for a forward walking path.

* * * * *